US012576059B2

(12) United States Patent
Shchepinov

(10) Patent No.: US 12,576,059 B2
(45) Date of Patent: Mar. 17, 2026

(54) METHODS AND COMPOSITIONS FOR TREATMENT OF INFLAMMATORY DISEASE

(71) Applicant: BioJiva LLC, San Jose, CA (US)

(72) Inventor: Mikhail S. Shchepinov, Oxford (GB)

(*) Notice: Subject to any disclaimer, the term of this patent is extended or adjusted under 35 U.S.C. 154(b) by 0 days.

(21) Appl. No.: 18/612,000

(22) Filed: Mar. 21, 2024

(65) Prior Publication Data

US 2025/0082596 A1 Mar. 13, 2025

Related U.S. Application Data

(63) Continuation of application No. 18/069,886, filed on Dec. 21, 2022, now abandoned.

(60) Provisional application No. 63/293,208, filed on Dec. 23, 2021, provisional application No. 63/292,388, filed on Dec. 21, 2021.

(51) Int. Cl.

| | |
|---|---|
| ***A61K 31/202*** | (2006.01) |
| ***A61P 11/00*** | (2006.01) |
| ***A61P 19/02*** | (2006.01) |
| ***A61P 29/00*** | (2006.01) |

(52) U.S. Cl.

CPC ............ *A61K 31/202* (2013.01); *A61P 11/00* (2018.01); *A61P 19/02* (2018.01); *A61P 29/00* (2018.01)

(58) Field of Classification Search

CPC .................................................... A61K 31/202

See application file for complete search history.

(56) References Cited

U.S. PATENT DOCUMENTS

| | | | |
|---|---|---|---|
| 2018/0339958 A1 | 11/2018 | Vidovic et al. | |
| 2019/0231733 A1* | 8/2019 | Shchepinov ........... | A61K 31/20 |
| 2021/0244637 A1 | 8/2021 | Shchepinov | |
| 2021/0251933 A1 | 8/2021 | Shchepinov | |
| 2021/0269376 A1 | 9/2021 | Vidovic et al. | |

FOREIGN PATENT DOCUMENTS

| | | |
|---|---|---|
| WO | WO-2018-094116 A1 | 5/2018 |
| WO | WO-2019-204582 A1 | 10/2019 |
| WO | WO-2020-102596 A1 | 5/2020 |
| WO | WO-2022-170217 A1 | 8/2022 |

OTHER PUBLICATIONS

Jun. 28, 2023—(WO) International Search Report and Written Opinion—App PCT/US2022/053687.

Das, Un et al. Can Bioactive Lipid Arachidonic Acid Prevent and Ameliorate COVID-19?, Medicina (Kaunas), vol. 56, No. 9, Aug. 19, 2020, doi: 10.3390/medicina56090418.

Chistyakov, DV et al. Deuterated Arachidonic Acids Library for Regulation of Inflammation and Controlled Synthesis of Eicosanoids: An In Vitro Study. Molecules, vol. 23, No. 12, Dec. 15, 2018, doi: 10.3390/molecules23123331, publication 3331, pp. 1-11.

Lamberson, CR et al. Unusual Kinetic Isotope Effects of Deuterium Reinforced Polyunsaturated Fatty Acids in Tocopherol-Mediated Free Radical Chain Oxidations. Journal of American Chemical Society, vol. 136, No. 3, Jan. 22, 2014, doi: 10.1021/ja410569g, pp. 838-841.

Luthria, DL et al. Synthesis of Ethyl Arachidonate-19, 19,20,20-d4 and Ethyl Dihomo-γ-linolenate-19, 19,20,20-d4. Lipids, vol. 28, No. 9, Sep. 1993, doi: 10.1007/BF02536242, pp. 853-856.

Molchanova, AY et al. Deuterated Arachidonic Acid Ameliorates Lipopolysaccharide-Induced Lung Damage in Mice. Antioxidants (Basel), vol. 11, No. 4, Mar. 31, 2022, doi: 10.3390/antiox11040681.

Adams J. D., "Chronic pain in the Skin and Neurogenic Inflammation", Journal of Alternative Complementary & Integrative Medicine, 2019, vol. 5, issue 3, article 073, 3 pp.; retrieved from the Internet: DOI: 10.24966/ACIM-7562/100073.

Mar. 22, 2023—(WO) International Search Report and Written Opinion—App PCT/US2022/053693.

* cited by examiner

*Primary Examiner* — Paul V Ward

(74) *Attorney, Agent, or Firm* — Young Basile Hanlon & MacFarlane, P.C.

(57) ABSTRACT

Disclosed herein are compositions and methods for controlling chronic inflammation in a patient. The compositions and methods employ D6-arachidonic acid or an ester thereof (D6-AA) as an anti-inflammatory agent that provides for significant reduction in inflammatory processes. In addition. The compositions of deuterated arachidonic acid or ester thereof comprise, on average, at least about 80% of the hydrogen atoms at each of the bis-allylic sites having been replaced by deuterium atoms and, on average, no more than about 30% of the hydrogen atoms at the mono-allylic sites having been replaced by deuterium atoms.

6 Claims, 13 Drawing Sheets

7,7-$D_2$-arachidonic acid 10,10-$D_2$-arachidonic acid 13,13-$D_2$-arachidonic acid 7,7,10,10-$D_4$-arachidonic acid 7,7,13,13-$D_4$-arachidonic acid 10,10,13,13-$D_4$-arachidonic acid 7,7,10,10,13,13-$D_6$-arachidonic acid

LIN

D2-LIN

ARA

D2-ARA

D6-ARA

METHODS AND COMPOSITIONS FOR TREATMENT OF INFLAMMATORY DISEASE

CROSS-REFERENCE

This application is a continuation of U.S. patent application Ser. No. 18/069,886, filed Dec. 21, 2022, which claims priority under 35 U.S.C. 119 (e) to U.S. Provisional Application No. 63/292,388 filed Dec. 21, 2021, and U.S. Provisional Application No. 63/293,208 filed Dec. 23, 2021, which are incorporated herein by reference in their entirety.

BACKGROUND

Arachidonic acid is an n-6 essential polyunsaturated fatty acid (PUFA) present in the human diet. It is an essential PUFA and a building block for phospholipids found in cellular membranes including neuronal cell membranes and neuronal organelles such as the mitochondria and the endoplasmic reticulum, where it is the dominant PUFA. The structure of arachidonic acid includes four double bonds in a 1,4-polyene configuration resulting in three bis-allylic positions and two mono-allylic positions that flank both ends of this configuration. The following structure provides an example of mono-allylic and bis-allylic positions in a 1,4-diene system.

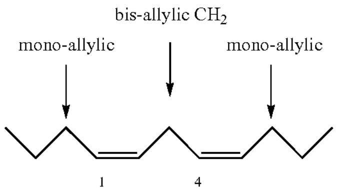

Arachidonic acid is readily oxidized at the bis-allylic sites either as a substrate of several enzymes (COX1, COX2, various LOX enzymes, and cytochromes P450, etc.) yielding multiple pro-inflammatory and pro-thrombotic eicosanoid mediators such as prostaglandins, leukotrienes and thromboxanes, or by reactive oxygen species (ROS) leading to further pro-inflammatory metabolites. In either case, such oxidation leads to inflammation in all tissues affected, including the lungs.

The pro-inflammatory and pro-thrombotic eicosanoid mediators then initiate further inflammatory cascades. Arachidonic acid's role in enzymatic generation of pro-inflammatory mediators is an important property of this PUFA. Indeed, replacing a portion of arachidonic acid in cell membranes by consuming fish rich in long chain n-3 polyunsaturated fatty acids, such as eicosapentaenoic acid and docosahexaenoic acid, has been reported to decrease inflammation merely by a mass balance approach. See, e.g., Calder, Biochem. Soc. Trans., 33 (part 2): 423-427 (2005).

In addition, it is well established that the etiology of many diseases involves an increase in the level of ROS which, in turn, initiates non-enzymatic chain reaction of arachidonic acid peroxidation in lipid membranes (LPO). This chain reaction leads to multiple toxic products including other pro-inflammatory mediators. While regulatory enzymes that neutralize oxidized products arising from LPO are present in cells, the increase in the amount of ROS generated by the disease overwhelms these enzymes and leads to an accumulation of pro-inflammatory mediators.

Both enzymatic and non-enzymatic oxidative transformations happen at any of the three bis-allylic sites within arachidonic acid as the carbon-hydrogen bond strength at these sites is the weakest within the molecule. The key rate limiting step for both types of transformation, termed hydrogen abstraction (a C—H bond cleavage), defines the rate of the whole process. That is to say that disease progression and, as a corollary, increases in inflammation is directly related to the rate of oxidation of the arachidonic acid (enzymatic oxidation) and oxidation of PUFAs in general (LPO oxidation).

Oxidative processes involving arachidonic acid are a key component in the generation of inflammatory processes in vivo. As is well established, chronic inflammation has deleterious impacts on patients. For example, the presence of chronic vascular inflammation has been implicated as a causative factor in coronary artery disease. Likewise, chronic arthritic conditions are associated with varying levels of pain, and disfigurement (especially in fingers) is also due to uncontrolled and chronic inflammatory processes.

Chronic pain associated with arthritis can be controlled in many cases with monoclonal antibodies such as TNF-alpha blockers. However, these antibodies carry substantial risks such as invasive fungal, bacterial, and viral infections, as well as lymphoma and other malignancies, some fatal, especially in children and adolescent patients. In many patients, such risks are unacceptable.

Accordingly, methods and compositions that control inflammation without the use of monoclonal antibodies would be of particular importance.

SUMMARY

Provided herein are compositions and methods for controlling chronic inflammation in a patient. The compositions and methods employ D6-arachidonic acid or an ester thereof (D6-AA) as an anti-inflammatory agent that provides for significant reduction in inflammatory processes. In addition, D6-AA has a long half-life such that when a therapeutic concentration is reached, the patient will experience long term control of chronic inflammatory process and long term control of the chronic pain.

In one embodiment, there is provided a method for controlling chronic inflammation in a patient which method comprises administering an effective amount of a composition comprising D6-AA to said patient for an effective period of time such that the accumulated D6-AA in the cellular membranes attenuates the inflammatory process, thereby controlling the chronic inflammation in the patient.

In one embodiment, a method for controlling chronic inflammation in a patient, as described herein, provides relief from chronic pain associated with the chronic inflammation.

In some embodiments, most or all of the hydrogens at the 7, 10 and 13 positions have been replaced as shown below:

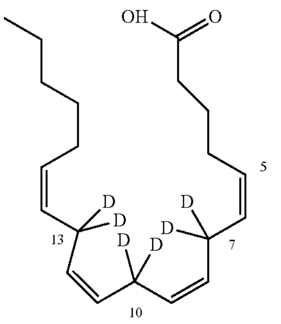 [SMILES: [2H]C([2H])(/C=C\CCCCC)/C=C\C([2H])([2H])/C=C\C([2H])([2H])/C=C\CCCC(=O)O]

In other embodiments, the methods described herein comprise a composition designated as D6-AA which composition comprises D6-arachidonic acid or an ester thereof that, on average, has at least about 80% of the hydrogen atoms at the bis-allylic sites replaced by deuterium atoms and, on average, no more than about 30% of the hydrogen atoms at the mono-allylic sites have been replaced by deuterium atoms. For example, in the case of an average of 85% deuteration of the 3 bis-allylic sites and 20% deuteration of the mono-allylic sites, the total amount of deuterium is (6×0.85)+(4×0.2)=5.9 (exclusive of the naturally occurring amount of deuterium) in each of the remaining methylene and methyl groups within the structure.

In one embodiment, there is provided a pharmaceutical composition comprising a pharmaceutically acceptable excipient and from about 10 mg to about 2,000 mg of a composition of D6-arachidonic acid or an ester thereof that, on average, has at least about 80% of the hydrogen atoms at each of the bis-allylic sites replaced by deuterium atoms and, on average, has no more than about 30% of the hydrogen atoms at the mono-allylic sites replaced by deuterium atoms.

In one embodiment, the chronic inflammation is vascular inflammation.

In one embodiment, the chronic inflammation is inflammation associated with arthritis. In one embodiment, the arthritis is rheumatoid arthritis. In one embodiment, the arthritis is osteoarthritis. In one embodiment, the chronic inflammation is neuroinflammation.

In one embodiment, the chronic inflammation is associated with a neurodegenerative disease.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 4 is the average) and an increase of the interalveolar septa thickness (FIG. 5 is the median; FIG. 6 is the average), which is likely associated with stronger edema and inflammatory infiltration. Mice that received D6-ARA exhibited alveolar lumen area and thickness consistent with controls. In general, the data of FIGS. 3-6 indicate a lesser degree of inflammatory lesion of the lungs after course of D-form compared to H-form. Preliminary data (not shown) indicates that D6-ARA had the best protective effect as compared to other deuterated PUFAs.

FIG. 7A shows various PUFAs. FIG. 7B is a schematic showing hydrogen abstraction off a bis-allylic hydrogen. FIG. 7C shows multiple products of non-enzymatic lipid peroxidation (LPO). FIG. 7D shows numerous products of enzymatic arachidonic acid oxidation.

FIG. 9A shows the graphs for visceral organs and skin. FIG. 9B shows graphs for neural tissue: whole brains and whole eyes. FIG. 9C shows lung arachidonic acid and conversion to longer chain PUFAs.

DETAILED DESCRIPTION

Figure 1:
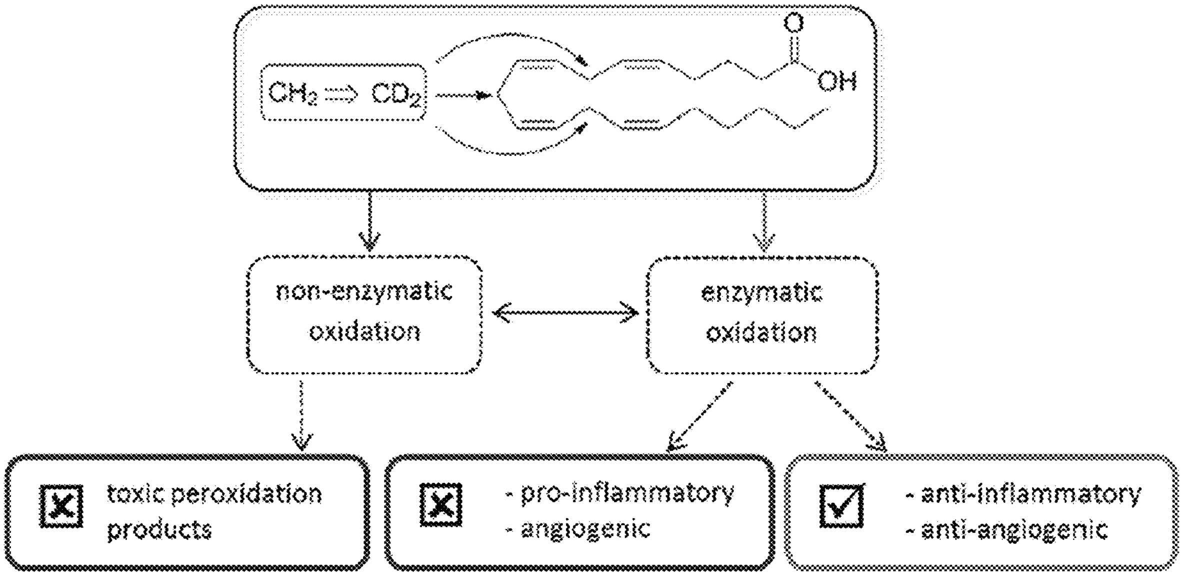
FIG. 1 Different bis-allylic sites may play a different role in oxidation of arachidonic acid.
Figure 2:
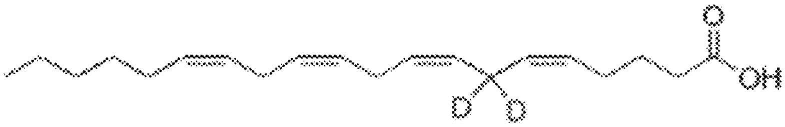
FIG. 2 Bis-allylic site-specific isotopically modified arachidonic acids. The bis-allylic positions are located at the C7, C10, and C13 positions. "D" represents deuterium.
Figure 2:
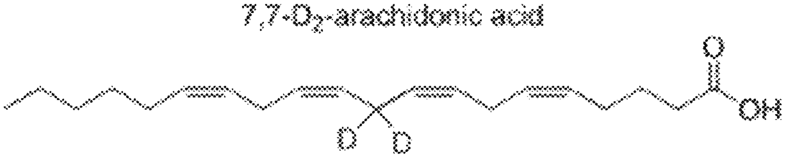
Figure 2:
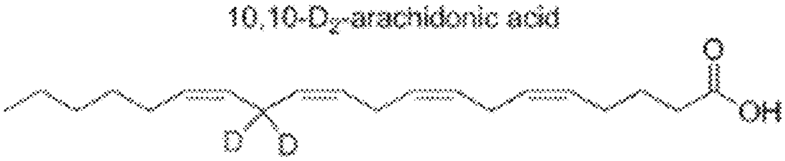
Figure 2:
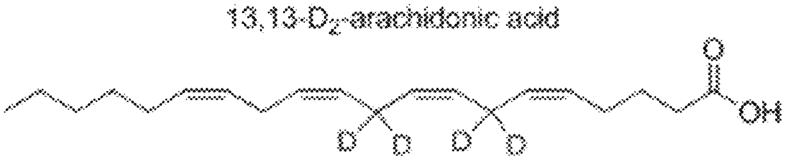
Figure 2:
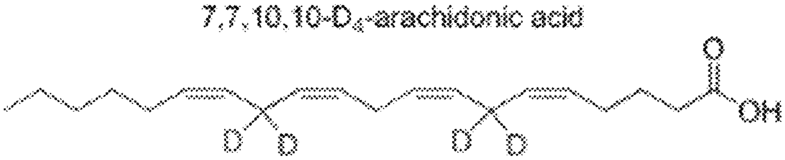
Figure 2:
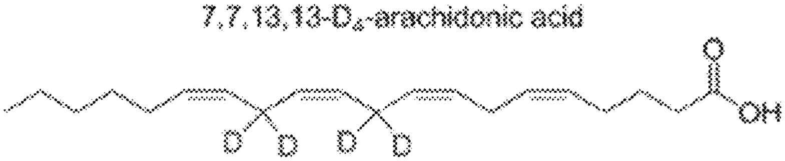
Figure 2:
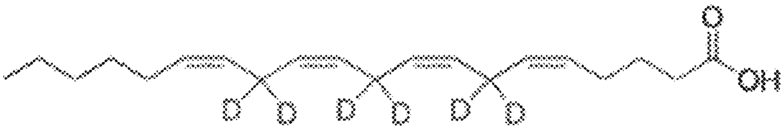
Figure 3:
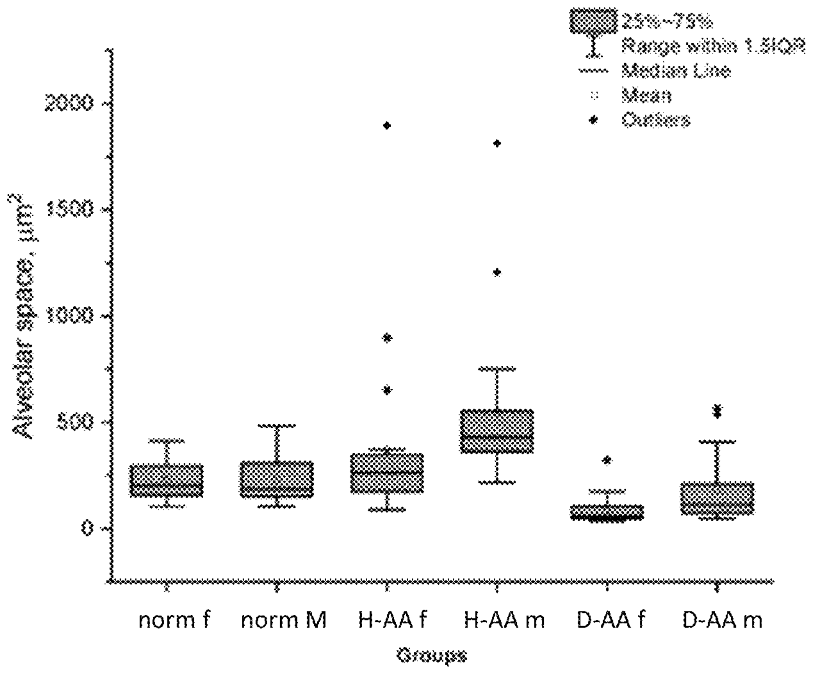
FIGS. 3-6 Groups of female (f) and male (m) mice received a 6-week course of dietary (H) AA or a 6-week course of deuterated arachidonic acid (D6-ARA, 15 mg/day) followed by single intranasal administration of LPS. Control mice (norm) did not receive the single intranasal administration of LPS. Mice that received dietary AA showed an increase of the alveolar lumen area (FIG. 3 is the median.
Figure 4:
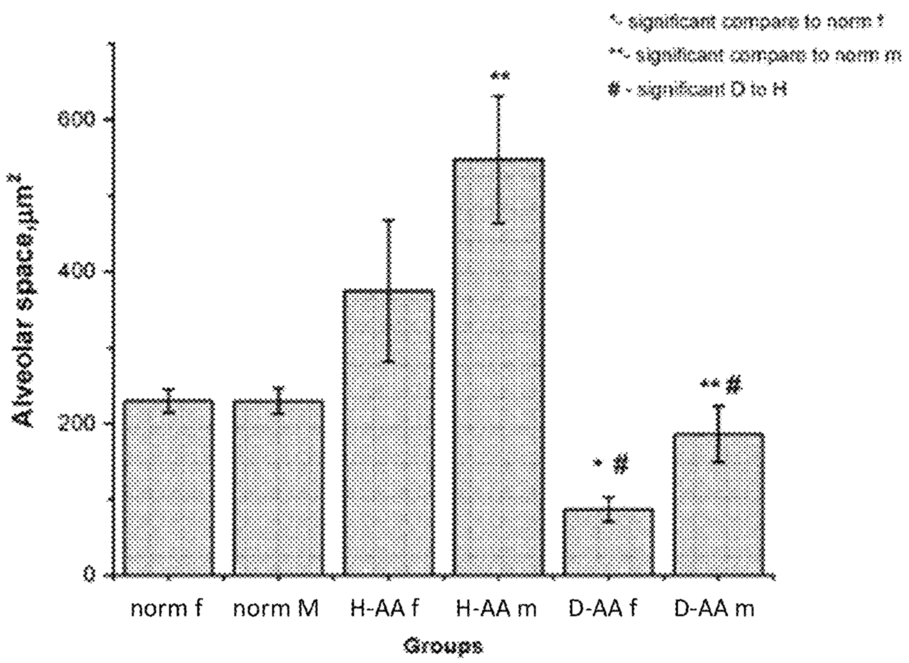
Figure 5:
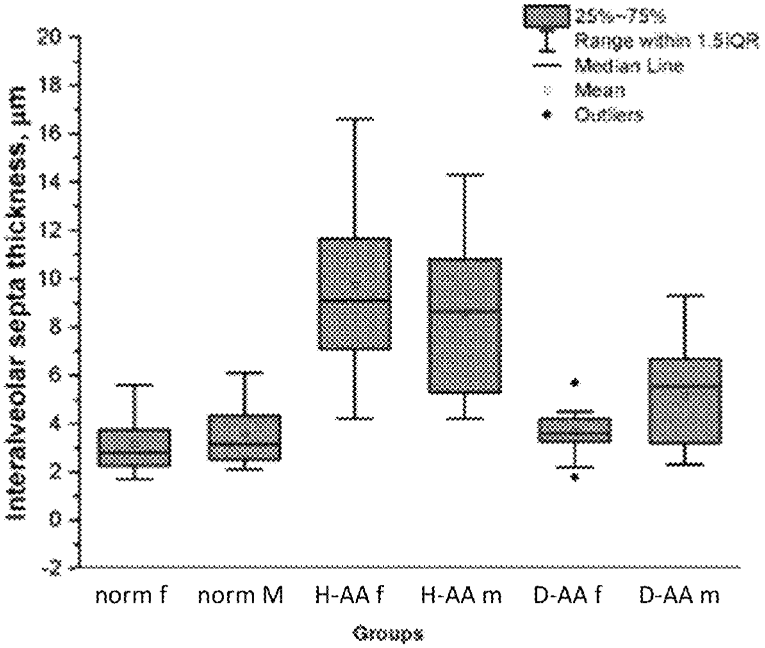
Figure 6:
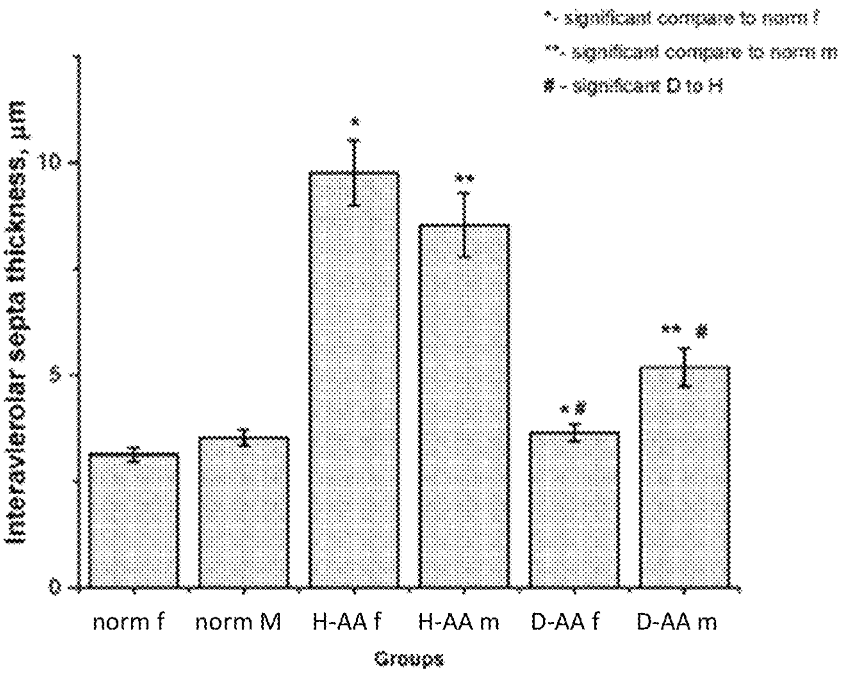

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Disclosed are methods for controlling inflammation in a patient. In one embodiment, the inflammation is due to intracellular accumulation of pro-inflammatory oxidized PUFA products.

Prior to discussing this invention in more detail, the following terms will first be defined. Terms that are not defined are given their definition in context or are given their medically acceptable definition.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the term "optional" or "optionally" means that the subsequently described event or circumstance can or cannot occur, and that the description includes instances where the event or circumstance occurs and instances where it does not.

As used herein, the term "about" when used before a numerical designation, e.g., temperature, time, amount, concentration, and such other, including a range, indicates approximations which may vary by (+) or (−) 15%, 10%, 5%, 1%, or any subrange or subvalue there between. Preferably, the term "about" when used with regard to a dose amount means that the dose may vary by +/−10%.

As used herein, the term "comprising" or "comprises" is intended to mean that the compositions and methods include the recited elements, but not excluding others.

As used herein, the term "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

As used herein, the term "consisting of" shall mean excluding more than trace elements of other ingredients and substantial method steps. Embodiments defined by each of these transition terms are within the scope of this invention.

The term "D6-arachidonic acid" or "D6-AA" means a composition that comprises, on average, at least about 4.8 to about 7.2 deuterium atoms in the arachidonic acid (excluding the ester portion thereof if employed). In one embodiment, this includes 7,7,10,10,13,13-D6-arachidonic acid or esters thereof. In another embodiment, this includes compositions of deuterated arachidonic acid or ester thereof that comprises, on average, at least about 80% of the hydrogen atoms at each of the bis-allylic sites having been replaced by deuterium atoms and, on average, no more than about 30% of the hydrogen atoms at the mono-allylic sites having been replaced by deuterium atoms.

In some embodiments, the amount of deuterium replacing hydrogen at the bis-allylic sites (7, 10 and 13) and at the mono-allylic sites (4 and 16) of arachidonic acid can be any one of the following (all percentages are on an average basis): at least about 85% deuterium at bis-allylic sites/no more than about 30% at mono-allylic sites; at least about 85% deuterium at bis-allylic sites/no more than about 25% at mono-allylic sites; at least about 85% deuterium at bis-allylic sites/no more than about 20% at mono-allylic sites; at least about 85% deuterium at bis-allylic sites/no more than about 10% at mono-allylic sites; at least about 85% deuterium at bis-allylic sites/no more than about 5% at mono-allylic sites; at least about 90% deuterium at bis-allylic sites/no more than about 30% at mono-allylic sites; at least about 90% deuterium at bis-allylic sites/no more than about 25% at mono-allylic sites; at least about 90% deuterium at bis-allylic sites/no more than about 20% at mono-allylic sites; at least about 90% deuterium at bis-allylic sites/no more than about 10% at mono-allylic sites; and at least about 90% deuterium at bis-allylic sites/no more than about 5% at mono-allylic sites.

As used herein and unless the context dictates otherwise, the term "an ester thereof" refers to a C1-C6 alkyl esters, glycerol esters (including monoglycerides, diglycerides and triglycerides), sucrose esters, phosphate esters, and the like. The particular ester group employed is not critical provided that the ester is pharmaceutically acceptable (non-toxic and biocompatible). In one embodiment, the ester is a C1-C6 alkyl ester which is preferably an ethyl ester.

As used herein, the term "phospholipid" refers to any and all phospholipids that are components of the cell membrane or other lipid membrane(s) within a cell. Included within this term are phosphatidylcholine, phosphatidylethanolamine, phosphatidylserine, and sphingomyelin. In the motor neurons, the cell membrane is enriched in phospholipids comprising arachidonic acid.

The term "bis-allylic site" refers to the methylene group ($CH_2$) separating two double bonds as depicted above.

The term "mono-allylic site" refers to the methylene group having an adjacent neighboring double bond on one side and a further methylene group on the opposite side as depicted above.

The term "cellular component" refers to any relevant structure found in human cells, including organelles having a lipid or phospholipid wall. Examples of such cellular components include, by way of example only, the mitochondria, the endoplasmic reticulum, golgi apparatus, nuclear membrane, and the like. Cellular components also include the cell membrane (plasma membrane).

The term "regulatory enzymes" as it relates to the neutralization of oxidized arachidonic acid products refer to those enzymes that are responsible to remove, alter, or destroy one or more of the oxidized arachidonic acid products from the cells to prevent the accumulation of these oxidized products within the cell. Examples of regulatory enzymes include glutathione peroxidase (GPx) enzymes, particularly GPx4. When these enzymes are impaired, such impairment results in the accumulation of lipid peroxides leading to loss of functionality, which is often death followed by cell death. Gaschler, et al., Biochem. Biophys. Res. Commun., 482(3):419-425 (2017).

The term "oxidized PUFA products" refer to any oxidized form of a polyunsaturated fatty acid as well as any and all metabolites formed from the oxidized PUFA including reactive aldehydes, ketones, alcohols, carboxyl derivatives which are either pro-inflammatory metabolites or are precursors of pro-inflammatory metabolites.

The term "neutralization of oxidized products" refers to enzymatic processes that remove, alter, or destroy toxic oxidized PUFA products from the cells to prevent the accumulation of these oxidized products within the cell. In healthy individuals, the neutralization of the oxidized PUFA products prevents accumulation of these products thereby assuring that dysfunctionality of cells especially neurodegenerative cells is controlled.

As used herein, the term "pathology of a disease" refers to the cause, development, structural/functional changes, and natural history associated with that disease. Included in the pathology of the disease is the reduction in cellular functionality. The term "natural history" means the progression of the disease in the absence of treatment per the methods described herein, for example, prior to the commencement of treatment as described herein.

As used herein, the term "chronic inflammation" refers to known conditions where inflammation plays a key role in the development and progression of chronic diseases including, but not limited to, autoimmune diseases, neurodegenerative diseases, metabolic disorders such as atherosclerosis and obesity, fibrosis, and cancer to name a few. Such diseases also include asthma, arthritis including rheumatoid arthritis, juvenile chronic arthritis, osteoarthritis, myossitis, Crohn's disease, gastritis, colitis, ulcerative colitis, inflammatory bowel disease, proctitis, pelvic inflammatory disease, systemic lupus, erythematosus, rhinitis, conjunctivitis, scleritis, chronic inflammatory polyneuropathy, Lyme's disease, psoriasis, dermatitis, and eczema, neurodegenerative diseases such as amyotrophic lateral sclerosis, Alzheimer's disease, Parkinson's disease, and multiple sclerosis to name a few. Such diseases are deemed chronic as the condition involved is either lifelong (after diagnosis) such as autoimmune diseases or which take substantially long periods of time to treat and resolve such as obesity.

As used herein, the term "control" or "controlling" as it relates to chronic inflammation means that the extent of inflammation arising from a chronic disease has been decreased or attenuated over time such that the degree of discomfort or pain arising in the patient is reduced. While the level of discomfort felt by a patient is personal and distinct from other patients suffering through the same disease, the decrease in inflammation can be measured by the extent of swelling, a decrease in C Reactive Protein (CRP), and other standards well known in the art. Preferably, a decrease of at least 15% and preferably at least 35% in CRP concentrations between start of therapy and 45 days or 90 days post start of therapy evidence control of the inflammation.

The term "therapeutic concentration" means an in vivo concentration of a deuterated arachidonic acid that controls chronic inflammation. In one embodiment, a concentration of D6-AA in red blood cells of at least about 1% and preferably at least from about 1.5% to about 6% based on the total amount of arachidonic acid found therein (including deuterated arachidonic acid) will be therapeutic.

As used herein, the term "patient" refers to a human patient or a cohort of human patients suffering from a neurodegenerative disease treatable by administration of a prodrug of deuterated arachidonic acid.

As used herein, the term "pharmaceutically acceptable salts" of compounds disclosed herein are within the scope of the methods described herein and include acid or base addition salts which retain the desired pharmacological activity and is not biologically undesirable (e.g., the salt is not unduly toxic, allergenic, or irritating, and is bioavailable). When the compound has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound has an acidic group, such as for example, a carboxylic acid group, it can form salts with metals, such as alkali and earth alkali metals (e.g., $Na^+$, $Li^+$, $K^+$, $Ca2^+$, $Mg^{2+}$, $Zn^{2+}$), ammonia or organic amines (e.g., dicyclohexylamine, trimethylamine, trimethylamine, pyridine, picoline, ethanolamine, diethanolamine, triethanolamine) or basic amino acids (e.g., arginine, lysine, and ornithine). Such salts can be prepared in situ during isolation and purification of the compounds or by separately reacting the purified compound in its free base or free acid form with a suitable acid or base, respectively, and isolating the salt thus formed.

Inflammation

Inflammation-related disorders represent a heterogeneous group of diseases that have a common underlying inflammatory pathology. For example, inflammation-related disorders include, but are not limited to, asthma, rheumatoid arthritis, juvenile chronic arthritis, osteoarthritis, myositis, Crohn's disease, gastritis, colitis, ulcerative colitis, inflammatory bowel disease, proctitis, pelvic inflammatory disease, systemic lupus erythematosus, rhinitis, conjunctivitis, scleritis, chronic inflammatory polyneuropathy, Lyme disease, psoriasis, dermatitis, eczema, autoimmune disorders, neurodegenerative disorders, and atherosclerosis.

Inflammation-related disorders often involve increased generation of ROS (reactive oxygen species) and lipid processing abnormalities (Winyard P G et al. Free radicals and inflammation. Burkhauser, Basel, 2000; Filippo et al., Journal of Alzheimer's Disease (2010); 20, S369-S379). The combination of ROS and lipid processing abnormalities leads to increased PUFA peroxidation that generates toxic reactive carbonyl compounds which inflict further damage at numerous other sites within the cell (Negre-Salvayre A et al., Br J Pharmacol 2008; 153:6-20). Consequently, the detection of oxidatively damaged biomolecules and the presence of ROS in inflammatory states both implicate elevated oxidative stress levels.

Lipid peroxidation is important in atherosclerosis and in worsening of initial tissue injury caused by ischemic or traumatic brain damage. Atherosclerosis is a lipid storage disorder associated with inflammatory response (Ross R, New Engl J Med. 1999; 340:115-127).

Oxidation of PUFA-rich low-density lipoprotein (LDL) was suggested to be a major risk factor for atherosclerosis and for hypertension associated with atherosclerosis. Angiotensin II (Ang-II) is involved in this process, enhancing macrophage lipid peroxidation both in vivo and in vitro (Keidar S. Life Sci. 1998; 63:1-11). Despite the importance of oxidative stress in the etiology of atherosclerosis, the success of antioxidant therapies aiming to reduce lipid peroxidation has so far been limited (Stocker R et al., Physiol Rev 2004; 84:1381-1478).

Rheumatoid arthritis may be associated with inflammation and PUFA peroxidation through a reperfusion injury mechanism. The synovial cavity normally has a negative pressure. When the joint is exercised, vascular patency is maintained, allowing for nutrition of the avascular cartilage. In rheumatoid synovitis, the cavity pressure is raised and upon movement this pressure exceeds the capillary perfusion pressure, causing collapse of the blood vessels. This leads to the production of multiple episodes of 'hypoxic-reperfusion injury' generating ROS which oxidize several targets, including, but not limited to: IgG, inducing rheumatoid factor production; Hyaluronan, leading to hyaluronan fragmentation products which may alter immune function; PUFAs, generating reactive carbonyls which alter T cell/macrophage interactions; and lipoproteins, leading to the production of monocyte chemotactic peptides. Progressive hypoxia alters immune function, predominantly by calcium mediated pathways. (Mapp P I et al., Br Med Bull 1995; 51:419-436). Various PUFA peroxidation products including, but not limited to, conjugated dienes, isoprostanes and reactive aldehydes such as HNE are detectable in plasma and synovial fluid of rheumatoid arthritis and osteoarthritis patients (Selley M L Annals Rheum Disease 1992; 51:481-484).

Oxidative damage is implicated in a wide variety of diseases such as mitochondrial diseases, neurodegenerative diseases, neurodegenerative muscle diseases, retinal diseases, energy processing disorders, kidney diseases, hepatic diseases, lipidemias, cardiac diseases, inflammation, and genetic disorders.

Oxidative stress at sites with chronic inflammation can also cause genetic changes. Reactive carbonyl products of PUFA peroxidation can react with DNA bases and change their complementarity pattern (Esterbauer H et al., Free Rad Biol Med 1991; 11:81-128). The development of mutations in the p53 tumor suppressor gene and other key regulatory genes can convert inflammation into chronic disease in rheumatoid arthritis and other inflammatory disorders (Tak P P et al., Immunology Today 2000; 21:78-82).

While the number of diseases associated with oxidative stress are numerous and diverse, it is well established that oxidative stress is caused by disturbances to the normal redox state within cells. An imbalance between routine production and detoxification of reactive oxygen species (ROS) such as peroxides and free radicals can result in oxidative damage to cellular structures and machinery. Under normal conditions, a potentially important source of ROS in aerobic organisms is the leakage of activated oxygen from mitochondria during normal oxidative respiration. Additionally, it is known that macrophages and enzymatic reactions also contribute to the generation of ROS within cells. Because cells and their internal organelles are lipid membrane-bound, ROS can readily contact membrane constituents and cause lipid oxidation. Ultimately, such oxidative damage can be relayed to other biomolecules within the cell, such as DNA and proteins, through direct and indirect contact with activated oxygen, oxidized membrane constituents, or other oxidized cellular components. Thus, one can readily envision how oxidative damage may propagate throughout a cell give the mobility of internal constituents and the interconnectedness of cellular pathways.

PUFAs endow mitochondrial membranes with appropriate fluidity necessary for optimal oxidative phosphorylation performance. PUFAs also play an important role in initiation and propagation of the oxidative stress. PUFAs react with ROS through a chain reaction that amplifies an original event (Sun M, Salomon R G, J. Am. Chem. Soc. 2004; 126:5699-5708). However, nonenzymatic formation of high levels of lipid hydroperoxides is known to result in several detrimental changes. Indeed, Coenzyme Q10 has been linked to increased PUFA toxicity via PUFA peroxidation and the toxicity of the resulting products (Do T Q et al., PNAS USA 1996; 93:7534-7539). Such oxidized products negatively affect the fluidity and permeability of their membranes; they lead to oxidation of membrane proteins; and they can be converted into a large number of highly reactive carbonyl compounds. The latter include reactive species such as acrolein, malonic dialdehyde, glyoxal, methylglyoxal, etc. (Negre-Salvayre A, et al., Brit. J. Pharmacol. 2008; 153:6-20). But the most prominent products of PUFA oxidation are alpha, beta-unsaturated aldehydes such as 4-hydroxynon-2-enal (4-HNE; formed from n-6 PUFAs like LA or AA), 4-hydroxyhex-2-enal (4-HHE; formed from n-3 PUFAs like ALA or DHA), and corresponding ketoaldehydes (Esterfbauer H, et al., Free Rad. Biol. Med. 1991; 11:81-128; Long E K, Picklo M J. Free Rad. Biol. Med. 2010; 49:1-8). These reactive carbonyls cross-link (bio) molecules through Michael addition or Schiff base formation pathways and have been implicated in a large number of pathological processes (such as those introduced above), age-related and oxidative stress-related conditions, and aging. Importantly, in some cases, PUFAs appear to oxidize at specific sites because methylene groups of 1,4-diene systems (the bis-allylic position) are substantially less stable to ROS, and to enzymes such as cyclooxygenases, cytochromes and lipoxygenases, than allylic methylenes.

Eicosanoids are important cell signaling molecules involved in an array of physiological and pathological processes, including various immune responses such as promoting inflammation, inhibiting inflammation, allergy, and fever. There are multiple oxidative and immune response related pathways in the biosynthesis of eicosanoids from arachidonic acid.

In one pathway, the enzyme 5-lipoxygenase (5-LO or ALOX5) converts arachidonic acid (ARA) into 5-hydroperoxyeicosatetraenoic acid (5-HPETE) and leukotriene A4 (LTA4), which is then converted into different leukotrienes (LTC4, LTD4, and LTE4) by downstream enzymes. LTC4, LTD4, and LTE4 are potent bronchoconstrictors and stimulators of mucus secretion in lung tissue and are known to promote hypersensitivity reactions in respiratory conditions such as asthma.

In another pathway leading to oxidative and inflammatory responses, 15-lipoxygenase (15-lipoxygenase 1, 15-LOX, 15-LOX1, or ALOX15) and 12-lipoxygenase (12-LOX or ALOX12) metabolize arachidonic acid to form 15(S)-hydroperoxyeicosatetraenoic acid (15(S)-HPETE) and 12(S)-hydroperoxyeicosatetraenoic acid (12(S)-HPETE). Both 15(S)-HPETE and 12 (S)-HPETE are further reduced by cellular glutathione peroxidase to their corresponding hydroxy analogs, 15-hydroxyicosatetraenoic acid (15(S)-HETE) and 12-hydroxyeicosatetraenoic acid (12(S)-HETE), respectively. 15(S)-HPETE and 15(S)-HETE are further metabolized to various bioactive products such as lipoxins, hepoxillins, eoxins, 8(S), 15(S)-diHETE, 5(S), 15(S)-diHETE and 15-oxo-eicosatetraenoic acid (15-oxo-ETE). The 12/15-lipoxygenase metabolities have been shown to have both pro- and anti-inflammatory properties.

In yet another pathway, COX1 and COX2 (also known as prostaglandin-endoperoxide synthase-1 (PTGS1) and PTGS2, respectively) initiates metabolization of arachidonic acid to a subclass of eicosanoids that includes prostaglandins (such as prostacyclins), and thromboxanes. Prostaglandins are mediators of inflammatory and anaphylactic reactions and thromboxanes are mediators of vasoconstriction and platelet aggregation, playing a major role in blood clotting.

In another pathway, cytochrome P450 enzymes metabolize arachidonic acid to EETs (epoxyeicosatrienoic acids). EETs can promote the active termination of inflammation through mediating a broad array of anti-inflammatory and pro-resolving mechanisms.

Prior studies have examined the relative enzymatic activity of cyclooxygenases and lipoxygenases upon isotopologues of arachidonic acid deuterated at bis-allylic positions, but these were mechanistic studies that did not use deuterated arachidonic acid in physiological or therapeutic amounts. One study tested the enzymatic activity of purified COX and LOX on different isotopologues of arachidonic acid, but the study did not test activity in cells. (Chistyakov, D., et al., Deuterated Arachidonic Acids Library for Regulation of Inflammation and Controlled Synthesis of Eicosanoids: An In Vitro Study, Molecules, 2018, 23:3331; which is hereby incorporated by reference in its entirety.) In another study, a macrophage cell-line was incubated with D-AA or normal AA, and cell-culture supernatants were analyzed for the amount of eicosanoids produced and secreted. However, this study used non-physiological conditions where arachidonic acid at a molar concentration of 25 micromolar was incubated with the cells for 24 hours, which resulted in incorporation of up to 90% of the arachidonic acid in cell membranes—a percentage unattainable by several-fold under physiological conditions. (Navratil, A. et al., Lipidomics Reveals Dramatic Kinetic Isotope Effects during the Enzymatic Oxygenation of Polyunsaturated Fatty Acids Ex Vivo). Thus, neither study has shown whether compositions comprising bis-allylic isotopically modified essential PUFAs, including arachidonic acid, can inhibit inflammation in vivo, which is important given the multiple metabolic pathways involving arachidonic acid and the potential pro- and anti-inflammatory effects resulting therefrom. Further, the purified enzymatic study (Chistyakov et al.) and the cell assay (Navratil et al.) both used very high concentrations of the designated AA species in the absence of other PUFAs and did not examine biologically relevant complex mixtures of fatty acids present at low concentrations, and enzymatic products derived therefrom, whether in in vitro or in vivo model systems.

Apart from the pro inflammatory enzymatic products of AA oxidation, the second major element of inflammation is the non-enzymatic chain reaction of PUFA damage, known as lipid peroxidation (LPO), which may be initiated by enzymes or by small molecule ROS. This pro-inflammatory non-enzymatic component is impervious to antioxidant approaches due to the structural aspects of the lipid bilayers making up membranes Inflammation associated LPO can be initiated through various mechanisms. (Zhang et al., Myeloperoxidase Functions as a Major Enzymatic Catalyst for Initiation of Lipid Peroxidation at Sites of Inflammation, J Blot Chem 2002 doi: 10.1074/jbc.M209124200).

Arachidonic acid is readily oxidized at the bis-allylic sites either as a substrate of several enzymes (COX1, COX2, various LOX enzymes, and cytochromes P450, etc.) yielding multiple pro-inflammatory and pro-thrombotic eicosanoid mediators such as prostaglandins, leukotrienes and thromboxanes, which then initiate further inflammatory cascades. Additionally, oxidation can occur via reaction with reactive oxygen species (ROS) leading to further pro-inflammatory metabolites. In either case, such oxidation leads to inflammation in all tissues affected, including the lungs.

Inflammation increases the level of reactive oxygen species (ROS) which in turn initiate non-enzymatic chain reaction of AA peroxidation in lipid membranes (LPO), leading to multiple toxic products. In addition, it is well established that the etiology of many diseases involves an increase in the level of ROS which, in turn, initiates non-enzymatic chain reaction of arachidonic acid peroxidation in lipid membranes (LPO). This chain reaction leads to multiple toxic products including other pro-inflammatory mediators. While regulatory enzymes that neutralize oxidized products arising from LPO are present in cells, the increase in the amount of ROS generated by the disease overwhelms these enzymes and leads to an accumulation of pro-inflammatory mediators.

Both enzymatic and non-enzymatic AA oxidative transformations happen at any of the three bis-allylic sites within the AA molecule as the carbon-hydrogen bond strength at these sites is the weakest within the molecule. The key rate limiting step for both types of transformation, termed hydrogen abstraction (a C—H bond cleavage), defines the rate of the whole process. That is to say that disease progression and, as a corollary, increases in inflammation is directly related to the rate of oxidation of the arachidonic acid (enzymatic oxidation) and oxidation of PUFAs in general (LPO oxidation). Thus, the present disclosure provides therapeutic methods based on the concept that AA oxidation plays a pivotal role in multiple aspects of inflammatory disorders, including cytokine storm and thrombotic complications.

COX and LOX inhibitors can be employed to down-regulate this process, with various efficacy. In contrast, the methods of the present disclosure rely on deuteration of the three oxidation prone sites within PUFA molecules, to substantially slow down the rate limiting step of oxidation (both enzymatic and non-enzymatic) via the isotope effect (IE). Made in high yield via a catalytic process, such D-PUFAs were tested in a lipopolysaccharide (LPS)-inflicted lung inflammation model in mice, a well-known lung inflammation model. (See Example 1.)

Intranasal administration of lipopolysaccharide (LPS), a bacterial endotoxin, has been shown to initiate a pro-inflammatory response in the lungs of mice. For example, the mouse LPS model has been used as a model for human acute lung injury (ALI), as the mouse lung parenchyma is damaged by the generation and release of proteases and reactive oxygen and nitrogen species produced by activated lung macrophages and transmigrated neutrophils in the interstitial and alveolar compartments. The end results are microvascular injury and diffuse alveolar damage with intrapulmonary hemorrhage, edema, and fibrin deposition (Johnson and Ward, J. Clin. Invest., (1974), 54:349-357; Flierl et al., Med. Hypothesis Res., (2006), 3:727¬738), which are also features in patients with ALI and the acute respiratory distress syndrome (ARDS) (Kabir et al., Shock, (2002), 17:300-303; Ward, Am. J. Pathol., (1996), 149:1081-1086). This LPS model recapitulates aspects of the inflammatory cascades that are associated with pulmonary inflammation associated with lung disease in humans, and so is useful as a screen for compounds that may disrupt these cascades and attenuate or abort the disease process. As discussed herein, in some embodiments, the D-PUFAs of the disclosure are administered to break the inflammatory cascade of specific cytokines and chemokines known to induce and amplify lung inflammation. Thus, for example, one can experimentally assess the efficacy of the D-PUFAs by examining whether the levels of inflammation associated markers are reduced. Two such markers, monocyte chemoattractant protein (MCP-1), and tumor necrosis factor alpha (TNF-a), are found to be associated with early and chronic infection and inflammation in humans and are mirrored in rodent models of airway inflammation including the mouse LPS pulmonary inflammation model.

The pro-inflammatory and pro-thrombotic eicosanoid mediators then initiate further inflammatory cascades. Arachidonic acid's role in enzymatic generation of pro-inflammatory mediators is an important property of this PUFA. Indeed, replacing a portion of arachidonic acid in cell membranes by consuming fish rich in long chain n-3 polyunsaturated fatty acids, such as eicosapentaenoic acid and docosahexaenoic acid, has been reported to decrease inflammation merely by a mass balance approach. See, e.g., Calder, Biochem. Soc. Trans., 33(part 2):423-427 (2005).

Oxidative processes involving arachidonic acid are a key component in the generation of inflammatory processes in vivo. As is well established, chronic inflammation has deleterious impacts on patients. For example, the presence of chronic vascular inflammation has been implicated as a causative factor in coronary artery disease. Likewise, chronic arthritic conditions are associated with varying levels of pain, and disfigurement (especially in fingers) is also due to uncontrolled and chronic inflammatory processes.

Pathology

The resulting pathology of chronic inflammatory diseases differs from the underlying etiology of the disease. That is to say that whatever divergent conditions trigger each of these diseases (the etiology), once triggered the pathology of these diseases involves the accumulation of pro-inflammatory oxidized PUFA products that are pro-inflammatory metabolites or are precursors to pro-inflammatory metabolites. As the amounts of oxidized products increases, the extent of the inflammatory response increases as such oxidized PUFA products activate the biological cascade leading to inflammation.

As per the above, the increasing concentration of oxidized PUFA products in cells correlates with the progression of the chronic disease that impacts these cells. The methods described herein provide for in vivo delivery of deuterated arachidonic acid to these cells, thereby limiting the amount of oxidized PUFA products generated as both LPO and enzymatic oxidation of arachidonic acid are reduced. Taken together, these two mechanisms either alone or in combination create oxidative stress on the cell. Reduction in the oxidative stress has a positive impact on treating the disease as well as the underlying inflammation. Thus, unlike monoclonal antibodies and other steroidal or non-steroidal anti-inflammatory products, the composition of this invention attenuates both the inflammatory component of the disease as well as addresses the underlying disease itself. This is because the ability of the disease to induce LPO and/or enzymatic oxidation of arachidonic acid is reduced by reinforcing the cell membranes of at-risk cells with D6-AA. In turn, this protects against cell lysis—a mechanism well known to release of pro-inflammatory cytokines and other intracellular components into the extracellular medium.

The origin of the oxidative stress varies due to differences in the underlying etiology but typically involve one or more different reactive oxygen species. Regardless of the differences in etiology, the production of oxidized PUFA products evidences an imbalance between routine production and detoxification (neutralization) of these oxidized products. The lipid membrane of the cell as well as that of the endoplasmic reticulum and mitochondria of neurons comprise arachidonic acid (a 20-carbon chain polyunsaturated fatty acid ("PUFA") having 4 sites of cis-unsaturation). Separating each of these 4 sites are 3 bis-allylic methylene groups. These groups are particularly susceptible to oxidative damage as compared to allylic methylene and methylene groups. Apart from leading to further membrane damage, oxidation of arachidonic acid reduces the local concentration of arachidonic acid and must be replaced. Thus, it is a double hit: a positive bioactive membrane component is converted to a toxic membrane component.

Given that certain cells have a high concentration of arachidonic acid in their lipid membranes, replacement of damaged or lost arachidonic acid in these membranes with deuterated arachidonic acid reinforces these structures in the cell and protects against formation of oxidized lipid products. For example, once a bis-allylic methylene group in one arachidonic acid is oxidized by a ROS, a cascade of further oxidation of other arachidonic acid groups in the lipid membrane occurs. This is because a single ROS generates oxidation of a first arachidonic acid component through a free radical mechanism which, in turn, can oxidize a neighboring arachidonic acid through the same free radical mechanism which yet again can oxidize another neighboring arachidonic acid in a process referred to as lipid chain auto-oxidation. The resulting damage includes a significant number of oxidized arachidonic acid products in the cell membrane and in the membrane of organelles. However, if an oxidized arachidonic acid is adjacent to the deuterated arachidonic acid, then that deuterated arachidonic acid acts as a chain-reaction terminator due to the much higher stability of the carbon-deuterium bond against oxidation as compared to the carbon-hydrogen bond.

Oxidized arachidonic acid and other oxidized PUFA products negatively affect the fluidity and permeability of cell membranes in the patient's neurons. In addition, they can lead to oxidation of membrane proteins as well as be converted into a large number of highly reactive carbonyl compounds. The latter include reactive species such as acrolein, malonic dialdehyde, glyoxal, methylglyoxal, etc. (Negre-Salvayre A, et al., Brit. J. Pharmacol. 2008; 153:6-20). The most prominent products of arachidonic acid oxidation are alpha, beta-unsaturated aldehydes such as 4-hydroxynon-2-enal (4-HNE; formed from n-6 PUFAs like LA or AA), and corresponding ketoaldehydes (Esterfbauer H, et al., Free Rad. Biol. Med. 1991; 11:81-128). As noted above, these reactive carbonyls cross-link (bio) molecules through Michael addition or Schiff base formation pathways, continuing the underlying pathology of the disease. Each of these metabolites derived from oxidized PUFAs are encompassed by the term "oxidized PUFA product(s)."

Disease Progression

Inflammation leads to an increase in inflammatory markers such as C-reactive protein (CRP) and Creatine Kinase (CK) [including CK-BB (brain), CK-MB (heart) and CK-MM (skeletal muscle)]. When a patient is diagnosed with a specific chronic inflammatory disease, the clinician can monitor the patient's CRP or the CK count to determine the efficacy of the therapy. The treatment described herein provides for a steady increase in the amount of deuterated arachidonic acid in the patient's cells over time until the concentration reaches an amount that reduces the amount of oxidative stress in the cells which results in inflammation.

Replacement of from about 1 to about 5 percent of the arachidonic acid components in a patient's red blood cells with the D6-AA occurs over about a twenty (20) to forty-five (45) day period during which a gradual decrease in the patient's CRP or CK can be observed. Typically, around day 30, the CRP or CK levels in the patient are lower to significantly lower than before the start of therapy evidencing the anti-inflammatory properties of the drug. As more D6-AA or an ester thereof is administered to the patient, its concentration in the cell will reach about 5% to about 20% or more in his/her red blood cells. In all cases, the in vivo concentration of D6-AA is measured by using red blood cells as a proxy for the cells at risk of or undergoing oxidative stress. The stated percent of D6-AA in these cells is measured based on the total weight of arachidonic acid in the red blood cells including D6-AA.

Without being limited to any theory, the progression of a chronic inflammatory disease correlates with the increase in oxidative stress in the cell including the accumulation of oxidized PUFAs. Therapeutic intervention as per the methods described herein limits further increases in oxidative stress and then reduces these levels to control the inflammation associated therewith. Regardless of the theoretical aspects, the examples provided below illustrate the significant reduction of inflammation achieved by D6-AA.

In one embodiment, the chronic inflammation is vascular inflammation.

In one embodiment, the chronic inflammation is inflammation associated with arthritis. In one embodiment, the arthritis is rheumatoid arthritis. In one embodiment, the arthritis is osteoarthritis. In one embodiment, the chronic inflammation is neuroinflammation.

Compound Preparation

Deuterated arachidonic acid is known in the art. For example, 7,7,10,10,13,13-D6-arachidonic acid is disclosed by Shchepinov, et al., Molecules, 28 (12): 31 et seq. (2018). Likewise, catalytic deuteration of arachidonic acid using a ruthenium catalyst resulting in about 80% or more deuteration of the bis-allylic sites and about 30% or less deuteration at the mono-allylic sites is disclosed by Shchepinov, et al., U.S. Pat. No. 10,730,821. Both of these references are incorporated herein by reference in their entirety. Still further, other deuterated arachidonic acid compounds are known in the art. Conversion of each of these PUFAs into the corresponding esters are well known in the art.

Methods

In one embodiment, the methods described herein comprise the administration of D6-AA or an ester thereof to a patient suffering from a chronic inflammatory disease. In vivo, the D6-AA slowly accumulates in the cells of the body including those that are subject to chronic inflammation. The clinician can monitor the progress of the therapy by measuring the amount of C-reactive protein (CRP) in the patient as chronic inflammatory diseases generate higher CRP levels and a reduction in that inflammation corresponds to a reduction in the CRP levels. In addition, the clinician can correlate lower CRP levels with increasing concentrations of D6-AA in red blood cells over time. As the concentration of D6-AA in red blood cells increases, CRP levels are expected to fall.

The methods described herein provide for rapid onset of a therapeutic concentration of deuterated arachidonic acid in vivo. In one embodiment, there is provided a method for reducing inflammation of a chronic inflammatory disease in an adult patient, the method comprising periodically administering D6-AA or an ester thereof to the patient with a dosing regimen that comprises a primer dose and a maintenance dose.

In an embodiment, the primer dose comprises periodic administration of deuterated arachidonic acid or an ester thereof. In an embodiment, the primer dose comprises at least about 10 milligrams of deuterated arachidonic acid or an ester thereof per day. In an embodiment, the primer dose comprises from about 10 milligrams to about 2 grams of deuterated arachidonic acid or an ester thereof per day. In an embodiment, the primer dose comprises from about 0.10 grams to about 1 gram. In an embodiment, the primer dose is continued for about 15 to about 50 days or from about 30 days to about 45 days, e.g., to rapidly achieve a therapeutic concentration of deuterated arachidonic acid in vivo, thereby reducing the rate of disease progression.

In an embodiment, after completion of the primer dose, the maintenance dose is periodically administered. In an embodiment, no more than about 65% of the loading dose of the deuterated arachidonic acid or an ester thereof per day is administered as a maintenance dose. In an embodiment, the maintenance dose is utilized to ensure that the therapeutic concentration of deuterated arachidonic acid is maintained in vivo such that a reduced rate of disease progression is maintained.

In one embodiment, said periodic administration of the loading dose comprises administration of from about 0.05 grams to about 2 grams of deuterated arachidonic acid or an ester thereof per day. In some embodiments, the loading dose is from about 0.05 grams to about 1.5 grams per day. In some embodiments, the loading dose is from about 0.10 grams to about 1.5 grams per day. In some embodiments, the loading dose is from about 0.10 grams to about 1.25 grams per day. In some embodiments, the loading dose is from about 0.10 grams to about 1 gram per day. In some embodiments, the loading dose is from about 0.10 grams to about 0.5 grams per day. The loading dose may be any value or subrange within the recited ranges, including endpoints.

In some embodiments, the loading dose is administered for at least 5 days per week, and preferably 7 days a week.

In one embodiment, the periodic administration of the maintenance dose of deuterated arachidonic acid or an ester thereof per day comprises no more than 65% or no more than 55% of the loading dose. In embodiments, the maintenance dose is administered per day, or at least 5 days per week, or at least once per week, or at least once per month. In another embodiment, the maintenance dose comprises no more than 35% of the loading dose which is administered at least once a month.

In one embodiment, the periodic administration of the maintenance dose is calibrated to be an amount of D6-AA or an ester thereof sufficient to replace the amount of deuterated arachidonic acid eliminated from the body.

In some embodiments, the loading dose is administered for between about one month and about 4 months. In some embodiments, the loading dose is administered for between about 1 month and about 2 months. In some embodiments, the loading dose is administered for about 1 month. The length of time may be any value or subrange within the recited ranges, including endpoints.

In some embodiments, the loading dose is administered between meals. In some embodiments, the dosing is done with food, e.g. during meals.

In some embodiments, whether the patient has a therapeutic level of D6-AA incorporated into the patient's cells is determined by simply measuring the patient's CRP levels. In some embodiments, the amount of D6-AA is determined based its concentration in red blood cells. In the event that the clinician determines that the patient is not responding as well as the clinician expected, an increase in either the loading dose or the maintenance dose can be made.

In some embodiments, whether the patient has a therapeutic level of deuterated arachidonic acid incorporated into the patient's neurons is determined. In some embodiments, the level of deuterated arachidonic acid is determined based on the amount of deuterated arachidonic acid in the patient's red blood cells. In some embodiments, the therapeutic target is at least about 6% or at least about 12% deuterated arachidonic acid, based on the total amount of arachidonic acid in the red blood cells (e.g., in a blood sample). In some embodiments, the therapeutic target is at least about 15%. In some embodiments, the therapeutic target is at least about 20%. In some embodiments, the therapeutic target is between about 12% and about 30% deuterated arachidonic acid, based on the total amount of arachidonic acid in the red blood cells (e.g., in a blood sample). In some embodiments, the therapeutic target is between about 12% and about 25% deuterated arachidonic acid, based on the total amount of arachidonic acid in the red blood cells (e.g., in a blood sample). In some embodiments, the therapeutic target is between about 12% and about 20% deuterated arachidonic acid, based on the total amount of arachidonic acid in the red blood cells (e.g., in a blood sample). In some embodiments, the therapeutic target is between about 15% and 25% deuterated arachidonic acid, based on the total amount of arachidonic acid in the red blood cells. In some embodiments, the therapeutic target is between about 15% and about 20% deuterated arachidonic acid, based on the total amount of arachidonic acid in the red blood cells (e.g., in a blood sample). The amount may be any value or subrange within the recited ranges, including endpoints.

In embodiments, D6-AA or an ester thereof (e.g., ethyl ester) may be administered using any dosing regimen. For example, D6-AA or an ester thereof may be administered daily, every two days, every 3 days, etc. In embodiments, D6-AA or an ester thereof may be administered for a first period of time (e.g., one week, 2 weeks, 3 weeks, 4 weeks or more), followed by a period of time where no D6-AA or an ester thereof is administered (e.g., 1 day, 2 days, 1 week or more). In embodiments, D6-AA or an ester thereof may be administered for a period of time until the therapeutic level is reached, and then administered less frequently. For example, D6-AA or an ester thereof may be administered daily until the therapeutic level is reached, and then administered every 2, 3, 4, 5, 6, or 7 days, or longer, to maintain the therapeutic level.

Combinations

The therapy provided herein can be combined with other treatments used to treat chronic inflammatory diseases. In one embodiment, D6-AA or an ester thereof can be used alone. Alternatively, D6-AA or ester thereof can be combined with 11,11-D2-linoleic acid or an ester thereof and/or with 8,8,11,11-D4-linoleic acid or an ester thereof. In vivo, a portion of the 11,11-D2-lineoleic acid is converted to 13,13-D2-arachidonic acid and a portion of the 8,8,11,11-D4-linoleic acid is converted to 10,10,13,13-D4-arachidonic acid.

In another embodiment, a combination therapy can employ a drug that operates via an orthogonal mechanism of action relative to the methods described herein. Suitable drugs for use in combination include, but not limited to, antioxidants such as edaravone, idebenone, mitoquinone, mitoquinol, vitamin C, or vitamin E, provided that none of these antioxidants interfere with the therapeutic action of the deuterated linoleic acid or ester thereof.

Pharmaceutical Compositions

The specific dosing of D6-AA or ester thereof is accomplished by any number of accepted modes of administration. As noted above, the actual amount of the drug used in a daily or periodic dose per the methods of this invention, i.e., the active ingredient, is described in detail above. The drug can be administered at least once a day, preferably once or twice or three times a day.

This invention is not limited to any particular composition or pharmaceutical carrier, as such may vary. In general, compounds of this invention will be administered as pharmaceutical compositions by any of a number of known routes of administration. However, orally delivery is preferred typically using tablets, pills, capsules, and the like. The particular form used for oral delivery is not critical but due to the large amount of drug to be administered, a daily or periodic unit dose is preferably divided into subunits having a number of tablets, pills, capsules, and the like.

Pharmaceutical dosage forms of a compound as disclosed herein may be manufactured by any of the methods well-known in the art, such as, by conventional mixing, tableting, encapsulating, and the like. The compositions as disclosed herein can include one or more physiologically acceptable inactive ingredients that facilitate processing of active molecules into preparations for pharmaceutical use.

The compositions can comprise the drug in combination with at least one pharmaceutically acceptable excipient. Acceptable excipients are non-toxic, aid administration, and do not adversely affect the therapeutic benefit of the claimed compounds. Such excipient may be any solid, liquid, or semi-solid that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Other suitable pharmaceutical excipients and their formulations are described in Remington's Pharmaceutical Sciences, edited by E. W. Martin (Mack Publishing Company, 18th ed., 1990).

The compositions as disclosed herein may, if desired, be presented in a pack or dispenser device each containing a daily or periodic unit dosage containing the drug in the required number of subunits. Such a pack or device may, for example, comprise metal or plastic foil, such as a blister pack, a vial, or any other type of containment. The pack or dispenser device may be accompanied by instructions for administration including, for example, instructions to take all of the subunits constituting the daily or periodic dose contained therein.

The amount of the drug in a formulation can vary depending on the number of subunits required for the daily or periodic dose of the drug. Typically, the formulation will contain, on a weight percent (wt. %) basis, from about 10 to 99 wt. % of the drug based on the total formulation, with the balance being one or more suitable pharmaceutical excipients. Preferably, the compound is present at a level of about 50 to 99 wt. %.

In one embodiment, the drug is encapsulated in a capsule without the need for any excipients such as stabilizers, antioxidants, colorants, etc. This minimizes the number of capsules required per day by maximizing the volume of drug in each capsule.

EXAMPLES

The present disclosure is further understood by reference to the following examples, which are intended to be purely exemplary of this invention. The present disclosure is not limited in scope by the exemplified embodiments, which are intended as illustrations of single aspects of this disclosure only. Any methods that are functionally equivalent are within the scope of this disclosure. Various modifications of this invention in addition to those described herein will become apparent to those skilled in the art from the foregoing description and accompanying figures. Such modifications fall within the scope of the appended claims. In these examples, the following terms are used herein and have the following meanings. If not defined, the abbreviation has its conventional medical meaning.

H-AA=Non-deuterated arachidonic acid (only with the natural abundance of deuterium)
H-LA=Non-deuterated linoleic acid (only with the natural abundance of deuterium)
D2-AA=11,11-D2-Arachidonic Acid
D6-AA=D-6 arachidonic acid having greater than 80% deuterium in the bis-allylic positions and less than 35% in the mono-allylic positions
h=hours
kg=kilograms
LPS=lipopolysaccharide
D2-LA=11,11-D2-Linoleic Acid (aka "drug")
LA=Linoleic Acid
LPO=Lipid peroxidation
M=Molar
mg=milligrams
ROS=Reactive Oxygen Species
μm=microns
$\mu m^2$=square microns Example 1: Control of LPS Induced Inflammation LPS administration is known to promote inflammation through various mechanisms including secretion of pro-inflammatory cytokines, eicosanoids and induction of ROS. This example employed LPS to ascertain the extent of inflammation arising from ROS induced oxidation of H-AA versus D-AA in the lungs of mice. Specifically, four groups of mice were used. The first group was control mice treated with H-LA control mice. The second group of mice received a 6-week course of D-LA. It is understood that in vivo conversion of a portion of both H-LA and D-LA occurs to provide for AA and 13,13-D2-AA respectively. The third group of mice received a 6-week course of H-AA. The fourth group of mice received a 6-week course of D-AA.

All groups then received a single intranasal administration of LPS to induce acute lung inflammation. The degree of the inflammatory response was based on the interalveolar septa distance where the larger the distance of the septa, the greater the degree of inflammation. The animals were sacrificed and the interalveolar septa distance was measured. Table 1 provides an average degree of spatial distance for the interalveolar septa for the results of all groups.

TABLE 1

| | H-LA | D-LA | H-AA | D-AA |
|---|---|---|---|---|
| Interalveolar space | 14.2 μm | 10.7 μm | 9.1 μm | 4.1 μm |

The above results evidence about a 25% reduction in the spatial distance for the interalveolar septa for the mice treated with D-LA relative to those treated with H-LA. However, the mice treated D-AA had almost a 60% reduction in the same spatial distance evidencing the benefits of D-AA in treating inflammation.

Example 2: Control of LPS Induced Inflammation-H-AA Versus D-AA

LPS administration was conducted as per Example 1 above except that four groups of mice were used. The first two groups (1 and 2) were control mice (male and female). The next two groups (3 and 4) of mice received a 6-week course of H-AA (male and female). Finally, the last two groups (5 and 6) of mice received a 6-week course of D6-AA (second group). Groups 3, 4, 5 and 6 then received a single intranasal administration of LPS to induce acute lung inflammation. The degree of the inflammatory response was determined per Example 1. The results of this experiment are set forth in Table 2.

TABLE 2

| | Control (F) | Control (M) | H-AA (F) | H-AA (M) | D-AA (F) | D-AA (M) |
|---|---|---|---|---|---|---|
| Interalveolar space | ~0.6 μm | ~0.7 μm | ~9.7 μm | ~8.1 μm | ~3.5 μm | ~5.0 μm |

The results of this experiment evidenced a statistically significant reduction in inflammation for both the male and female mice using D-AA as compared to D-LA.

Next, the height and distance of the interalveolar septa was determined to provide for the surface area of the inflammation. The results of this evaluation are set forth in Table 3.

TABLE 3

| | Control (F) | Control (M) | H-AA (F) | H-AA (M) | D-AA (F) | D-AA (M) |
|---|---|---|---|---|---|---|
| Interalveolar surface area | ~215 $\mu m^2$ | ~215 $\mu m^2$ | ~380 $\mu m^2$ | ~540 $\mu m^2$ | ~90 $\mu m^2$ | ~190 $\mu m^2$ |

The degree of alveolar lumen area changes in both groups of animals depended on gender. This indicator, regardless of the form of acid (H or D), in females was significantly lower than in males. However, for the male mice that received the D-form, the severity of changes in thickness of interalveolar septa was significantly higher than that of females, correlating well with human cases (females less affected). In general, the data obtained is in agreement with the data above which indicated less inflammation in the lungs with treatment with the D-6 AA as compared to H-AA independent of the sex of the mice.

The following examples, i.e., Examples 1a, 2a, and 3a, represent a more complete recitation of Examples 1, 2, and 3 respectively.

Example 1a: Administration of D-AA in a Mouse Model of Lung Inflammation

LPS treatment promotes inflammation through various mechanisms including secretion of pro-inflammatory cytokines, eicosanoids and induction of ROS. Following induction by the intranasal administration of LPS, an acute lung inflammation quickly follows. In mice receiving a 6-week course of dietary (H) AA followed by single intranasal administration of LPS, the thickness of the interalveolar septa was significantly increased, which is likely associated with stronger edema and inflammatory infiltration. Such a pronounced inflammatory infiltration of the interalveolar septa contributed to their destruction and more frequent formation of emphysema foci in this group. At the same time, lungs of mice that received the D-form were characterized by decrease in alveoli lumens, which may be associated with a lower (compared with the H-form) frequency of emphysematous transformation of the lungs. (See FIGS. 3-6.)

The degree of alveolar lumen area changes in both groups of animals depended on gender. This indicator, regardless of the form of acid (H or D), in females was significantly lower than in males. Besides of this among the mice that received the D-form, the severity of changes in thickness of interalveolar septa was significantly higher in males compared to females, correlating well with human cases (females less affected). In general, the data obtained indicate a lesser degree of inflammatory lesion of the lungs after course of D-form compared to H-form. Preliminary data (not shown) also indicates that D6-AA (7,7,10,10,13,13-D6-arachidonic acid) provides a better therapeutic effect as compared to other deuterated essential PUFAs. Table 4. below summarizes the data underlying FIGS. 3-6.

TABLE 4

| | Group, gender | | | | | | |
|---|---|---|---|---|---|---|---|
| Morphological criterion | Control, males 1 | Control, females 2 | H-ara + LPS, males 3 | H-ara + LPS, females 4 | D-ara + LPS, males 5 | D-ara + LPS, females 6 | Significance Criterion, p |
| Alveolar lumen area (25%; 75%), $\mu m^2$ | 185.35 (149.45; 308.70) | 201.15 (156.00; 296.30) | 431.1 (362.75; 554.1) | 263.7 (173.85; 348.45) | 112.1 (73.1; 209.95) | 57.4 (46.15; 104.4) | $p_{1-2}$ = 0.7327<br>$p_{1-3}$ = 0.0000<br>$p_{2-4}$ = 0.2068<br>$p_{1-5}$ = 0.0225<br>$p_{2-6}$ = 0.0000<br>$p_{3-5}$ = 0.0000<br>$p_{4-6}$ = 0.0000 |
| Partition thickness Me (25%; 75%), $\mu m^2$ | 3.15 (2.5; 4.35) | 2.8 (2.25; 3.75) | 8.65 (5.3; 10.8) | 9.1 (7.1; 11.65) | 5.55 (3.2; 6.7) | 3.6 (3.25; 4.2) | $p_{1-2}$ = 0.1284<br>$p_{1-3}$ = 0.0000<br>$p_{2-4}$ = 0.0000<br>$p_{1-5}$ = 0.0011<br>$p_{2-6}$ = 0.0473<br>$p_{3-5}$ = 0.0018<br>$p_{4-6}$ = 0.0000 |

Oral data from human dosing in ongoing clinical trials show an impressive safety record for a similar D-PUFA drug which is a metabolic precursor to AA. The expected safety of a D-PUFA drug combined with the convenience of oral dosing of D-PUFA gel caps warrant further studies of D-PUFAs as an approach for anti-inflammatory, and possibly preventative, therapy against COVID-19 induced cytokine storm and thrombosis events. Other PUFA emulsions such as IntraLipid are formulated in emulsions and dosed I.V. at multiple grams per day safely. One could imagine such a formulation could enable rapid, bolus dosing of the drug upon treatment onset, followed up by lipid gel cap oral dosing of D-AA as a continuing therapy. These data present a rationale for further research on deuterated PUFA technology as an approach to COVID inflammation-associated therapy and other inflammation-associated conditions.

Example 2a: In Vitro Assay for Inflammation

In vitro cell-based assays for inflammation are well known in the art. These assays include such examples as e-selectin (also named Endothelial Leukocyte Adhesion Molecule or ELAM) and C-reactive protein (CRP). The ELAM assay can measure in vitro activity of test compounds in reducing expression of ELAM in activated endothelial cells.

For example, activated endothelial cells are created by adding known activators such as lipopolysaccharides, TNF, or IL-1 (3 to rat intestinal MVEC cells. Activated cells are incubated with an isotopically modified PUFA such as a deuterated PUFA ("D-PUFA") (0.01, 0.1, 1.0, 10.0, or 100 μM of D-PUFA and 1:1 or different ratio combinations of D-PUFA mixtures, e.g. D2-LA, D4-ALA, et al., see e.g. species that fall within Formula (1) supra) or "H-PUFA" (H-PUFA means not deuterated or tritiated) (0.01, 0.1, 1.0, 10.0, or 100 UM of LA, ALA, et al., and corresponding ratio combinations of non-deuterated mixtures) for 24, 48, and 72 hours. Activated cells are known to produce ELAM, which can be measured using, for example, an E-selectin monoclonal antibody-based ELISA assay. D-PUFA treated cells are expected to produce lower amounts of ELAM as compared to cells treated with H-PUFA.

Similarly, a CRP assay can be used to measure the in vitro activity of test compounds in reducing expression of CRP in Human Hep3B epithelial cells. For example, activated epithelial cells are created by adding known activators such as lipopolysaccharides, TNF, or IL-1 (3 to Human Hep3B epithelial cells. Activated cells are incubated with D-PUFA (0.01, 0.1, 1.0, 10.0, or 100 μM), and different ratio combinations of different D-PUFAs) or H-PUFA (0.01, 0.1, 1.0, 10.0, or 100 M of LA, ALA, and corresponding combinations of H-PUFAs) for 24, 48, and 72 hours. Activated cells are known to produce CRP, which can be measured with a CRP ELISA assay. D-PUFA treated cells are expected to produce lower amounts of CRP as compared to cells treated with H-PUFA.

Example 3a: In Vivo Assay for Inflammation

In vivo evaluation of anti-inflammatory activity can be determined by well characterized assays measuring Carrageenan-Induced Paw Edema and by Mouse Ear Inflammatory Response to Topical Arachidonic Acid. (See Gabor, M., Mouse Ear Inflammation Models and their Pharmacological Applications, 2000, which is incorporated herein by reference). Carrageenan-Induced Paw Edema is a model of inflammation that measures time-dependent edema formation following carrageenan administration into the intraplantar surface of a rat paw. Groups (8-9 animals/group) of 8-week old Wistar albino rats are supplemented with D-PUFA (see, e.g., species of Formula (1)) (0.01, 0.1, 1.0, 10.0, and 100 mg/kg), and different combinations of D-PUFAs (e.g., 1:1 ratio of two types of D-PUFAs) or H-PUFA (0.01, 0.1, 1.0, 10.0, and 100 mg/kg) and different combinations of H-PUFA corresponding to the different combination of D-PUFA, as the only PUFA source for a period of 8 weeks. Following the supplementation period, the rats are lightly anaesthetized under isofluorane and receive a subplantar injection of 50 μL saline containing 1% w/v carrageenan. Paw volumes are determined using a water plethysmometer and compared to paw volume prior to carrageenan administration. Volumes are measured at 0.5, 1, 2, 3, 4, and 5 hr. Edema can be calculated as the increase in paw volume divided by the starting paw volume. Rats supplemented with D-PUFA are expected to have lower levels of edema as compared to Rats supplemented with H-PUFA.

Additionally, the application of arachidonic acid (AA) to the cars of rats is known to produce immediate vasodilation and erythema, followed by the abrupt development of edema, which should be maximal at 40 to 60 min. The onset of edema is believed to coincide with the extravasations of protein and leukocytes. After one hour the edema should wane rapidly and the inflammatory cells should leave the tissue so that at 6 hours the ears will have returned to near normal. Groups (8-9 animals/group) of 8-week old male rats are supplemented with D-PUFA (see, e.g., species of Formula (1)) (0.01, 0.1, 1.0, 10.0, and 100 mg/kg of D-PUFA, and different combinations of D-PUFAs (e.g., 1:1 ratio of two types of D-PUFAs) or H-PUFA (0.01, 0.1, 1.0, 10.0, and 100 mg/kg) and different combinations of H-PUFA corresponding to the different combination of D-PUFA, as the only PUFA source for a period of 8 weeks. Following the supplementation period, arachidonic acid is applied to the cars of the rats and vasodilation, erythema and edema is measured as a function of time. Rats supplemented with D-PUFA are expected to have lower levels of edema as compared to Rats supplemented with H-PUFA.

Example 4: Collagen-Induced Arthritis Model

Groups (8-9 animals/group) of DBA/1 mice 8-10 weeks of age are supplemented with D-PUFA (see, e.g., species of Formula (1)) (0.01, 0.1, 1.0, 10.0, and 100 mg/kg of D-PUFA, and different combinations of D-PUFAs (e.g., 1:1 ratio of two types of D-PUFAs) or H-PUFA (0.01, 0.1, 1.0, 10.0, and 100 mg/kg) and different combinations of H-PUFA corresponding to the different combination of D-PUFA, as the only PUFA source for a period of 8 weeks. Mice are then injected with 100 μg bovine type II collagen in Freund's complete adjuvant (FCA) intradermally at the base of the tail and monitored by daily examination for the onset of disease, which is recorded. D-PUFA treated mice are expected to have a delayed onset, it any onset, of arthritis symptoms as compared to H-PUFA treated mice.

Alternatively, forty-five DBA/1 mice 8-10 weeks of age are injected with 100 μg bovine type II collagen in Freund's complete adjuvant (FCA) intradermally at the base of the tail and monitored by daily examination for the onset of disease, which is recorded. At the first appearance of clinical evidence of arthritis, mice are divided randomly into one of three treatment groups: 1) control; 2) D-PUFA (0.01, 0.1, 1.0, 10.0, and 100 mg/kg), and 1:1 or different combinations of different species of D-PUFA) treated; or 3) H-PUFA (0.01, 0.1, 1.0, 10.0, and 100 mg/kg), and 1:1 or different combinations of H-PUFA corresponding in type to D-PUFA combinations. The severity of arthritis in the affected paw is graded according to an established score system as follows: 0 (normal joint), 1 (mild/moderate visible edema and swelling), 2 (severe edema with distortion of paw and joint) and 3 (deformed paw or joint with ankylosis). The sum of the scores for all four paws in each mouse is used as an arthritis index (maximum score/mouse=12) to represent overall disease severity and progression in the animal. Animals re clinically assessed for disease five times per week until ten weeks after disease onset, and paw measurements are made three times per week. Arthritic paws without signs of disease at any time following treatment are considered in remission. All mice are pre-bled prior to the start of the trial, subsequently at onset of arthritis, two weeks post onset, four weeks post onset and at the completion of the trial. Sera obtained from each group is stored at −80° C. until needed. ELISA assays are performed to determine total anti-collagen antibody levels in mouse CIA. D-PUFA treated animals are expected to have reduced signs of arthritis as compared to H-PUFA treated animals and control animals.

Example 5: Deuterated Arachidonic Acid Ameliorates Inflammation-Induced Lung Damage in Lipopolysaccharide-Treated Mice Excessive inflammatory damage to the lung tissue during bacterial or viral infections occurs with the involvement of dysregulated eicosanoid axis and hindered repair of complex components of cellular membranes and secreted surfactant proteolipids. Acute respiratory distress syndrome (ARDS) is an aggravating condition; ARDS is associated with aging is a contributor to mortality in as many as 40% of deaths. ARDS is often caused by bacterial or viral pneumonia. In rodents, ARDS is usually modeled as acute lung injury (ALI) by instillation of live bacteria (*S. pneumoniae* or *P. aeruginosa*) or non-specific damaging factors like ozone. Bacterial ALI can be modeled by a sterile single dose challenge with *E. coli* lipopolysaccharide (LPS).

Figure 7A:
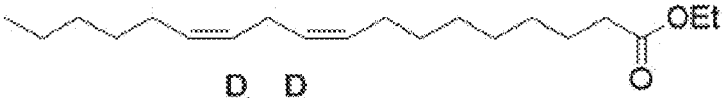
FIGS. 7A-D show various molecules and reactions relating to PUFAs.
Figure 7A:
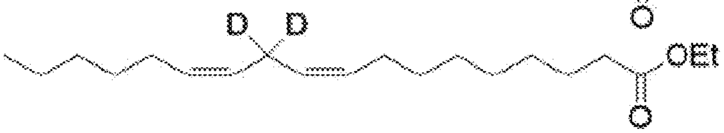
Figure 7A:
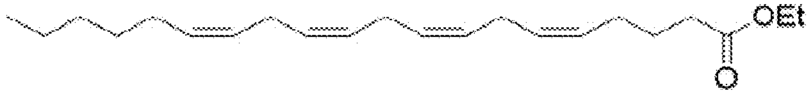
Figure 7A:
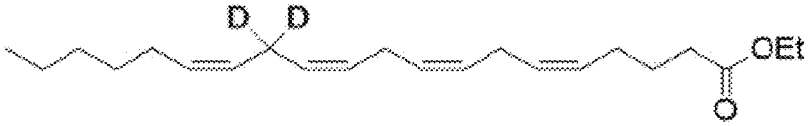
Figure 7A:
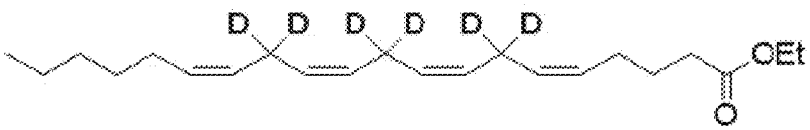
Figure 7B:
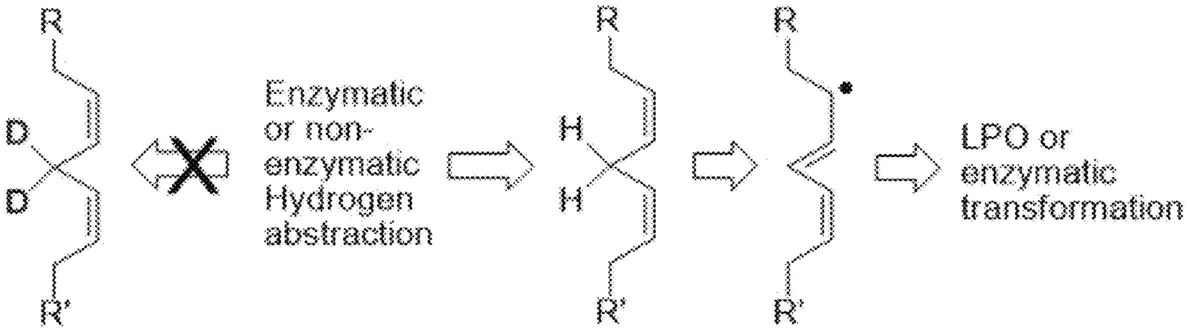
Figure 7C:
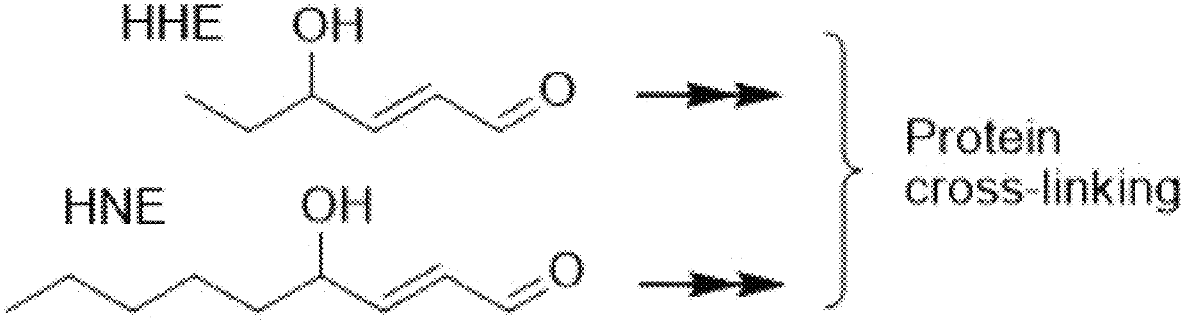
Figure 7D:
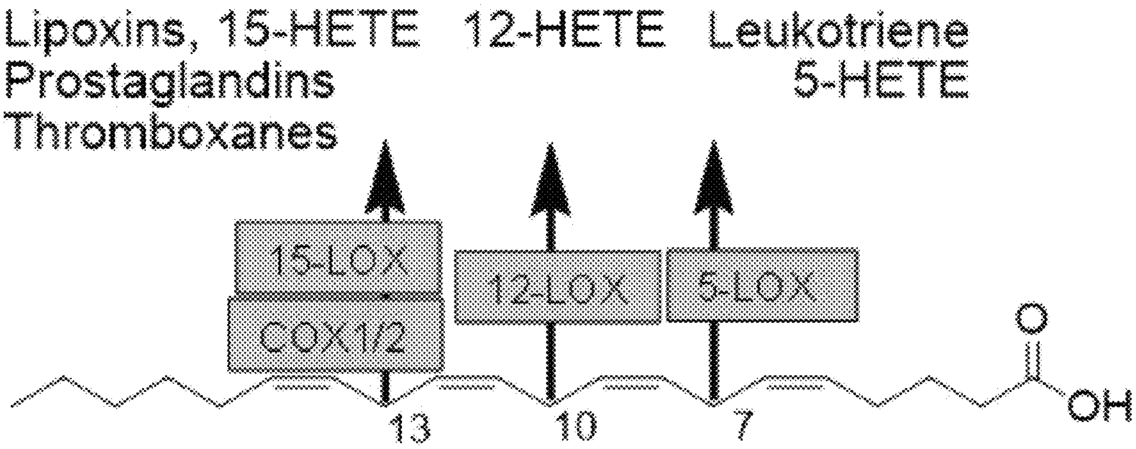

FIG. 7A shows various PUFAs that are used. LA, linoleic acid; D2-LA, 11,11-D2-linoleic acid; AA, arachidonic acid; D2-AA, 13,13-D2-arachidonic acid (a product of in vivo enzymatic elongation/extension of D2-LA); D6-AA, 7,7,10,10,13,13-D6-arachidonic acid. FIG. 7B is a schematic showing hydrogen abstraction off a bis-allylic hydrogen, the key rate-limiting step of PUFA oxidation (both enzymatic and LPO), is inhibited by deuteration. FIG. 7C shows multiple products of non-enzymatic LPO include reactive carbonyls like HHE and HNE, which can covalently cross-link biomolecules. FIG. 7D shows numerous products of enzymatic AA oxidation are mostly pro-inflammatory and pro-thrombotic.

This approach uses the deuteration of the three oxidation prone sites within AA molecule, to substantially slow down the rate limiting step of oxidation (both enzymatic and non-enzymatic) via the isotope effect (IE). Here the effects are shown of dietary arachidonic acid (H-AA) or its hexa-deuterated form (D-AA) on the lungs and gastrointestinal tract in healthy and LPS-treated mice.

Materials and Methods

Bis-allylic D-PUFAs were produced by total synthesis and by catalytic deuteration.

In Vivo Model and Sampling Protocols

Mouse diet was from Research Diets (New Brunswick, NJ) based on fat-free AIN-93G. Fat was added at 11.3% by weight total fat and 0.25% either normal H-AA or D-AA respectively (Table 5).

TABLE 5

Fat content in mice diets

| Fat composition of research diets | H-AA (green dye) | D-AA (pink dye) |
|---|---|---|
| Saturated fat, % | 7.75 | 7.75 |
| High oleic sunflower, % | 3.1 | 3.1 |
| H-linolenic (ethyl linolenate), | 0.2 | 0.2 |
| AA ethyl ester, % | 0.25 (H-AA) | 0.25 (D-AA) |

Male and Female BALB/c and C57BL/6 mice were provided with standard environmental conditions i.e., 22±1° C., 55±5% humidity and 12 h light/dark cycle with free food and water access. At the age of six weeks, animals were split into 8 groups (n=160 total, 20 of each gender) and were continuously fed ad libitum on the diet containing either H-AA or D-AA for 2, 4, 6 or 8 weeks at the daily rate of ca. 5 g of diet per mouse for the duration of the study. The other two groups of animals (n=40, 20 of each gender) received neither PUFA-enriched diets nor LPS served as controls. The body weight and food intake were measured once a week. After completing the appropriate diet course, half of the mice in each group (10 females and 10 males) (i) underwent the procedure of bronchoalveolar lavage (BAL) to accomplish cytological smears, (ii) were subjected to tissue harvesting and collection of colon contents (after humane euthanasia with lethal dose of sodium thiopental, 100 mg/kg intravenously). On the ninth week of this diet course, the other half of the group was administered 1 mg/kg of intranasal (IN) LPS from *Escherichia coli* O111:B4 (Sigma Aldrich) 24 hours prior to BAL and subsequent euthanasia. 40 D-AA fed animals (20 males, 20 females) were switched to the H-AA diet for washout experiments.

Bronchoalveolar Lavage (BAL) Fluid Collection

Briefly, lungs were lavaged three times using three aliquots of 1 ml 0.15 M NaCl under deep anesthesia (sodium thiopental). Each lavage consisted of slow infusion and gentle aspiration of saline via tracheal cannula. Three recovered lavages were combined. The samples were centrifuged for 7 minutes at 400 g and 4° C. in a microcentrifuge with a F241.5P rotor (Beckman Coulter, USA). The supernatants were collected and stored frozen at −80° C. no longer than one month before further analysis.

Cell Differential Counts in BAL

Cell differential counts were performed on smear slides from resuspended cell pellets of BAL, using commercially available May-Grünwald-Giemsa staining kits. All slides were evaluated in a light microscope (Optec BK5000) at ×200 magnification. These cell counts such as lymphocytes, neutrophils, plasmacytes and macrophages were obtained from 10 fields of each slide.

Histological Analysis

Lung, stomach and colon samples were fixed with 4% formaldehyde (freshly prepared from paraformaldehyde), paraffin embedded and cut into 2-4 μm sections. For routine histology, all fixed tissue sections were stained with hematoxylin-eosin (H&E). All slides were evaluated at 10 fields each using a Genetic Pro Bino light microscope (A) and photographed with a digital camera (Delta Optical). Stomach and colon tissue sections were analyzed for signs of active and chronic inflammation, formation of lymph follicles, and hyperplasia of epithelial cells. The severity of lung injury was scored according to lung pathological changes, including interalveolar and perivascular hemorrhages, peri-vascular and peribronchial infiltration, perivascular edema, thickness of alveolar wall, alveolar space value, and emphysematous transformations. Lung tissue samples were additionally stained with commercially available Martius Scarlet Blue (MSB) stain kit (Avantik, USA) for fibrin visualization. The presence of homogeneous fibrin masses of yellow, pink or red color in the lung blood vessels were interpreted as thrombotic masses.

Analysis of Microflora

Colon contents of euthanized mice were collected for microbial community analyses, immediately frozen and stored at −20° C. until analyzed. The samples were slowly thawed at +4° C., serial dilutions (10-3) were prepared, plated on specific media and incubated at 37° C. as follows. Microaerophylic flora: Enterococci-Enterococcal agar, 48 h; lactobacilli—Lactobacagar, 3 days; bifidobacteria—*Bifidum*-medium, 5 days, at 37° C.; Aerobes: Staphylococci—medium N10 for 48 h, coliforms—Endo medium for 48 h at 37° C., yeast-like fungi—Saburo agar, 48 h. These specific media were purchased from GNC PMIB (Obolensk, Russia). At the end of the specified incubation periods, colony forming units (CFU) were counted.

Cytokine Measurements with Enzyme-Linked Immunosorbent Assay (ELISA)

Cell free BAL fluid supernatants as well as colon tissue samples were analyzed using commercially available Mouse IL-1B ELISA Kit (R&D systems, Lot P265854, USA) and the Biotek ELx-808 microplate reader (Biotek, USA) according to the instructions recommended by the manufacturer).

AA Isotopic Analysis (GC-MS/MS)

The relative ratio of H-AA to D-AA was determined by gas chromatography (GC) coupled to chemical ionization mass spectrometry. Briefly, freshly harvested samples were homogenized and extracted by the Bligh and Dyer method, placed in tubes, solvent evaporated, blanketed with dry nitrogen, sealed, and shipped to Austin (TX) for further sample preparation and analysis. Dried samples were converted to fatty acid methyl esters (FAME) by a one-step method of hydrolysis and methylation. Solvent-medicated (SM) chemical ionization was performed with $CH_3CN$ as reagent using a Shimadzu GCMS-TQ8040 (Columbia, MD) instrument with a BPX70 capillary column (25 m×0.22 mm×0.25 μm; Trajan, Pflugerville, TX). D-AA was chromatographically separated from H-AA. Total ion chromatograms were used to integrate peak areas.

Statistical Analysis

Experimental data were processed using the Statistica 10.0 software package. Data are shown in graphs as medians and interquartile ranges (Me; Q25%; Q75%). For intergroup comparison, the nonparametric Kruskell-Wallace test was used, with adjustment for multiple comparisons. Differences were considered statistically significant at with p equal to or less than 0.05.

Effect of D-Linoleic Acid (D2-LIN) on the Lungs in LPS-Treated Mice

In our first experiment, we evaluated the effects of linoleic acid (LA) supplementation on interalveolar septa thickness and AS in LPS-treated mice. In this experimental setting, mice (six weeks old, both genders) received PUFAs of interest once per day via oral gavage 50 μL per mice. Upon completion of PUFA-treatment mice were intranasally administered with 1 mg/kg of LPS and sacrificed 24 hours later for lung histology. The results (FIG. 8) demonstrate a small, but statistically significant decrease of alveolar wall thickness in D2-LA mice when compared to H-LA group. This could be explained by a more pronounced hyperallergic response of lungs to H-LA compared with D2-LA. LPS treatment revealed signs of hyperplasia of bronchial epithelium and its hypersecretion, focal perivascular and peribronchial lymphoid infiltrates together with the presence of serous edema. Histologically, this effect was accompanied by inflammatory cells infiltration through alveolar walls.

Since D2-LA is partially converted to D2-AA by the action of fatty acid desaturases 1 and 2 (FADS1 and FADS2) and by fatty acid elongase 5 (ELOVL5), we hypothesized that the aforementioned effects of D-PUFA can be attributed to deuteration of AA, and that direct D6-AA supplementation would be much more efficient than that with D2-LA.

Figure 8:
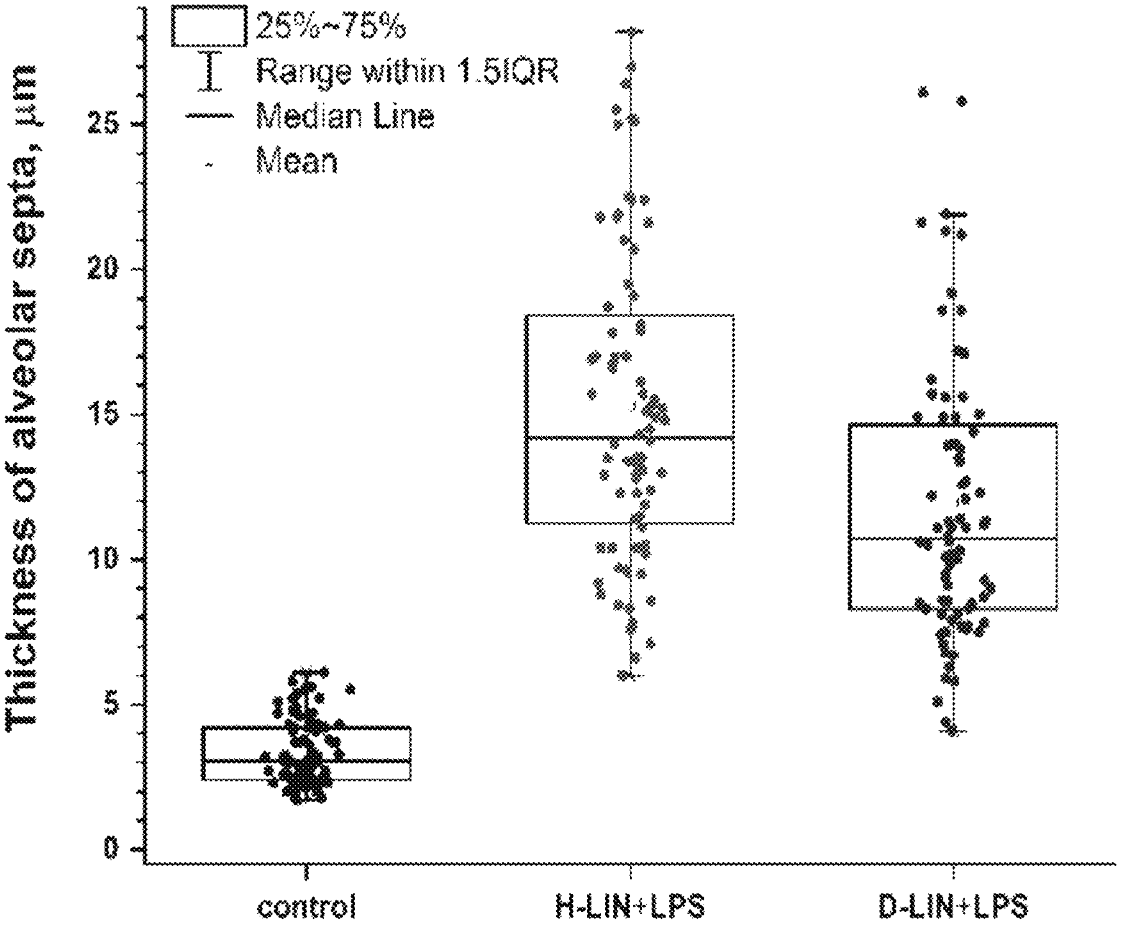
FIG. 8 shows the thickness of interalveolar septa of BALB/c mice treated with PUFAs.

FIG. 8 shows the thickness of interalveolar septa (μm) of BALB/c mice after 6 weeks of H- or D-forms of linoleic acid (H-LA and D2-LA) followed by single intranasal administration of lipopolysaccharide. *—$p \leq 0.05$, compared H-LA versus D2-LA mice.

Pharmacokinetic Aspects of Dietary Supplementation of D-AA in Healthy Mice

As the first step to test this hypothesis, we studied the metabolic effect of such a dietary supplementation. We determined the actual content of D-AA and then performed a washout experiment after a long period of supplementation by switching from D-AA to H-AA diet by MS analysis of several mouse tissues in the AA-diet fed mice. Twelve weeks of dosing on D-AA results in more than 60% incorporation of the deuterated form (around 90% of all AA as D6-AA except for brain which had 70% of all AA as D6-AA) (FIG. 9)

Figure 9A:
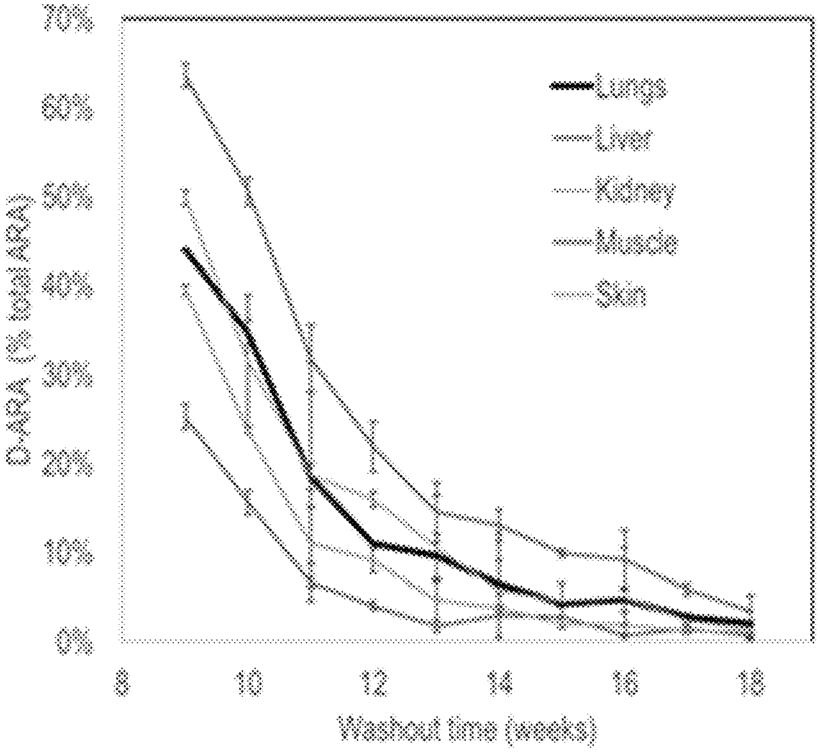
FIGS. 9A-9C shows deuterated arachidonic acid as a % of all arachidonic acid at eight weeks dosing and washout over the subsequent 9 weeks with H-AA feeding.
Figure 9B:
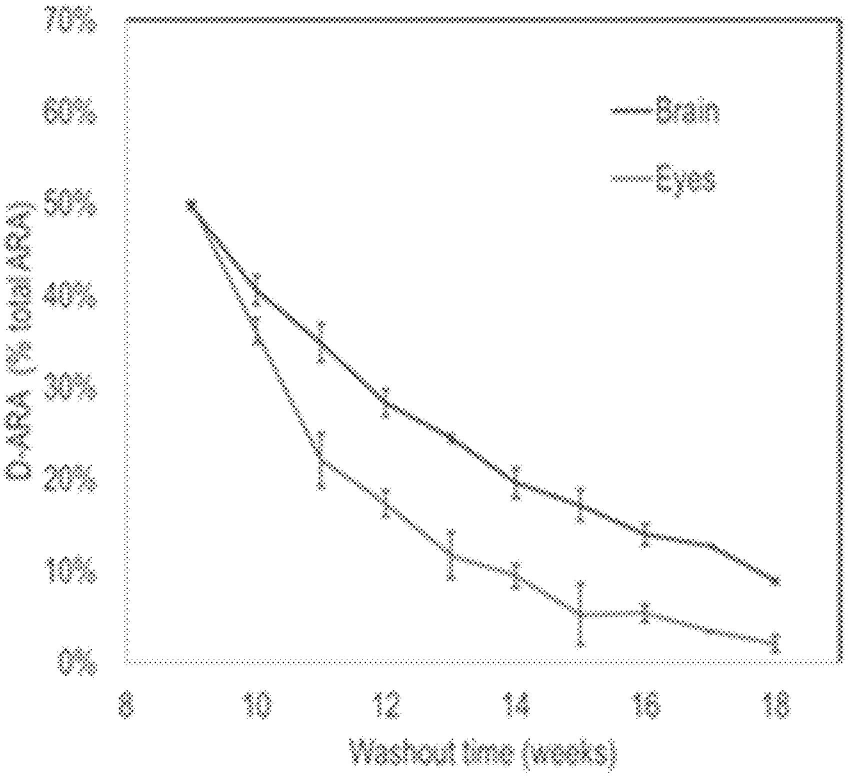
Figure 9C:
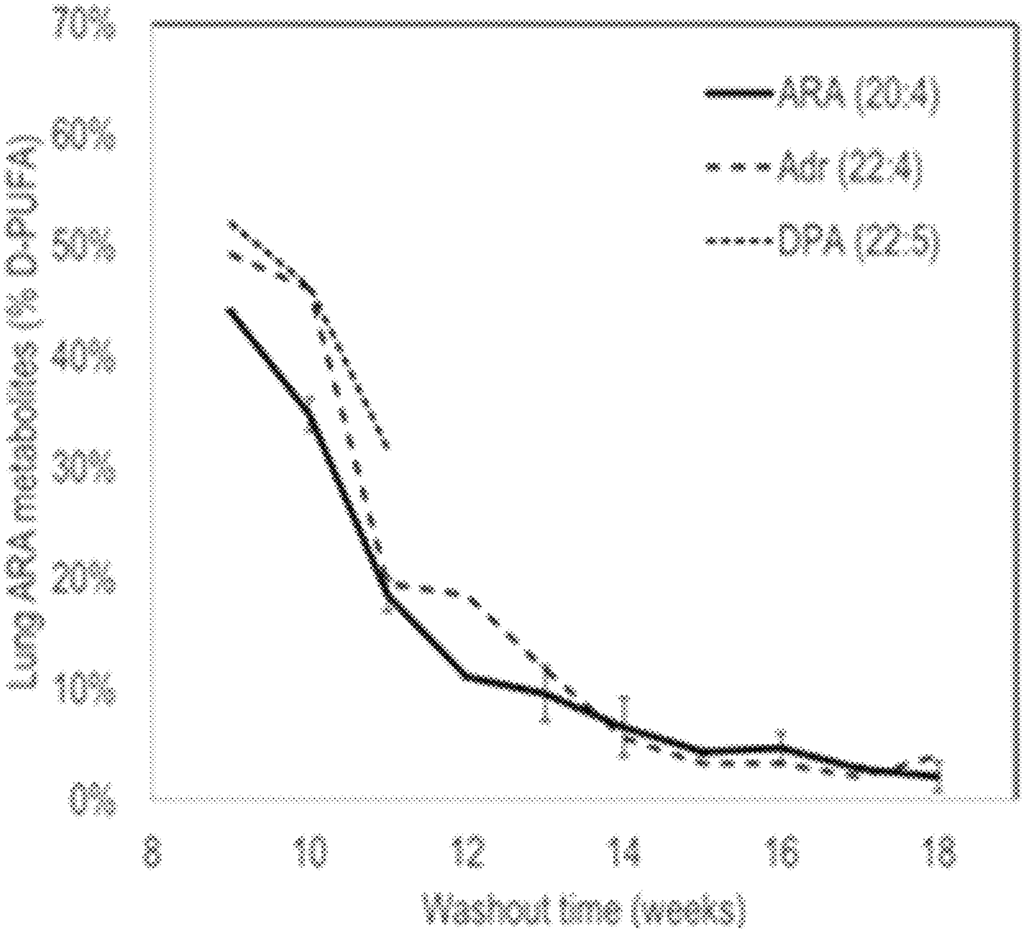

FIGS. 9A-9C shows D-AA as a % of all AA at eight weeks dosing and washout over the subsequent 9 weeks with H-AA feeding. FIG. 9A shows the graphs for visceral organs and skin. Lung incorporated about 45% D-AA. FIG. 9B shows graphs for neural tissue: whole brains and whole eyes. Both incorporated about 50% D-AA. Washout from eyes was more rapid than brain. FIG. 9C shows lung D-AA and conversion to longer chain PUFA adrenic acid (22:4) by elongation and docosapentaenoic acid (DPA, 22:5) by desaturation. All PUFA followed similar washout kinetics.

Brain fatty acid metabolism tends to be distinct from that in the visceral tissues, including in overall turnover. Neural PUFA are uniquely unsaturated, with AA and omega-3 docosahexaenoic acid (DHA) together comprising about 40% of all brain fatty acids, while linoleic acid is below 1%. Lungs are similar to other tissues.

Effects of H-AA and D-AA on Animal Health

H-AA and D-AA were well tolerated without apparent adverse reactions. Consumption of the diets for 2, 4, 6 or 8 weeks did not lead to significant changes in the level of IL-1β in BAL fluid or large intestine homogenates of conventionally healthy mice, regardless of gender. Macroscopically, the lungs of all groups were normal at the time of euthanasia. Cellular infiltration in the BAL was not significantly affected by either of AA-rich diets. After 8 weeks of feeding AA-rich diets, the number of lymphocytes increased compared to the control. The number of inflammatory cells in cytological smears of lavage was not significantly different between dietary consumption of H- and D-forms.

The effects of the AA diets on interalveolar septa thickness depended on duration and were affected by deuteration. The average thickness of mice interalveolar septa after H-AA and D-AA diets given for 2 or 4 weeks did not significantly differ. On the other hand, alveolar walls of healthy males and females after 8 weeks of H-AA consumption were significantly ($p \leq 0.05$) thicker compared to those in respective D-AA-cohorts. No relevant changes of alveolar spaces were observed for AA or for D6-AA diets. Analysis of the composition of the intestinal microflora, as well as the enzyme immunoassay of the interleukin level in lavage and intestinal homogenates, did not reveal any significant differences between mice on the diets regardless of the dietary course duration (data not shown).

Effect of D-AA on the Response to LPS

We challenged mice fed AA-diets for 6 weeks using LPS treatment. Twenty-four hours after exposure to LPS, the lung tissue showed intense perivascular, peribronchial, and septal inflammatory infiltration, with a predominance of lymphocytes and macrophages. Perivascular edema, signs of thrombosis, alveolar wall thickening, irregular distribution of air spaces, and focal areas of alveolar hemorrhage were also observed. We preferred intranasal administration to the more extreme intratracheal route that induces IL-1β which in turn amplifies inflammation making it difficult to distinguish between the early and late consequences of the LPS challenge. Indeed, 24 hours after intranasal administration of LPS at a dose of 1 mg/kg, there was no significant increase in the IL-1B content in BAL fluid or colon homogenates compared to animals not treated with LPS regardless of type or duration of the diets. Intranasal LPS 24 hours post administration increased neutrophils in BAL fluid in all treated groups regardless of gender or form of AA diets. Counts of other inflammatory cells in LPS-treated animals changed similarly with these of non-treated mice and were characterized by significantly higher numbers of lymphocytes after 8 weeks of consuming either H- or D-AA compared to 2 weeks course of H-AA No statistically significant differences between the effects of H- and D-AA were noted for any of the analyzed inflammatory cell types, regardless of gender and LPS treatment.

Figure 10A:
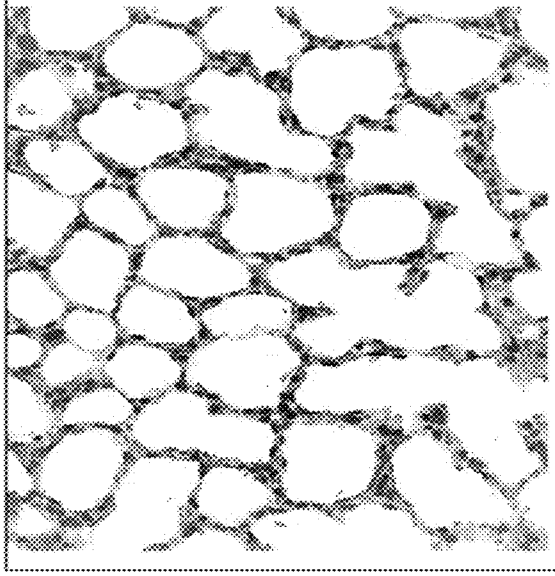
FIGS. 10A-C show histological evaluation of the effect of intranasal administration of lipopolysaccharide on the lungs of treated male mice.
Figure 10B:
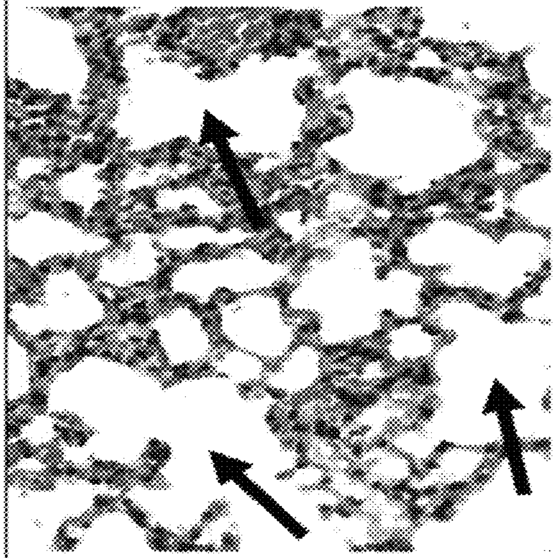
Figure 10C:
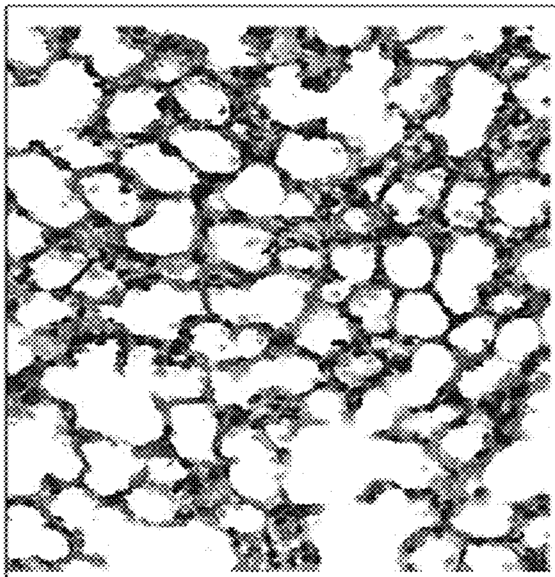

In mice receiving a 6-week course of dietary H-AA followed by single intranasal administration of LPS, the thickness of the interalveolar septa was significantly increased, which is likely associated with more edema and greater inflammatory severity accompanied by immune cell infiltration. At the same time, lungs of some mice that received H-AA and challenged with LPS showed areas of emphysematous transformation (FIGS. 10A-10C). FIGS. 10A-10C show histological evaluation of the effect of intranasal administration of lipopolysaccharide on the lungs of H-AA and D-AA treated male mice. FIG. 10A corresponds with normal mice lungs; FIG. 10B correspond with lung of mice that are LPS-treated on H-AA diet; FIG. 10C corresponds with lungs of mice that are LPS-treated on D-AA diet. The arrow in the figures point to emphysematous areas.

Figure 11:
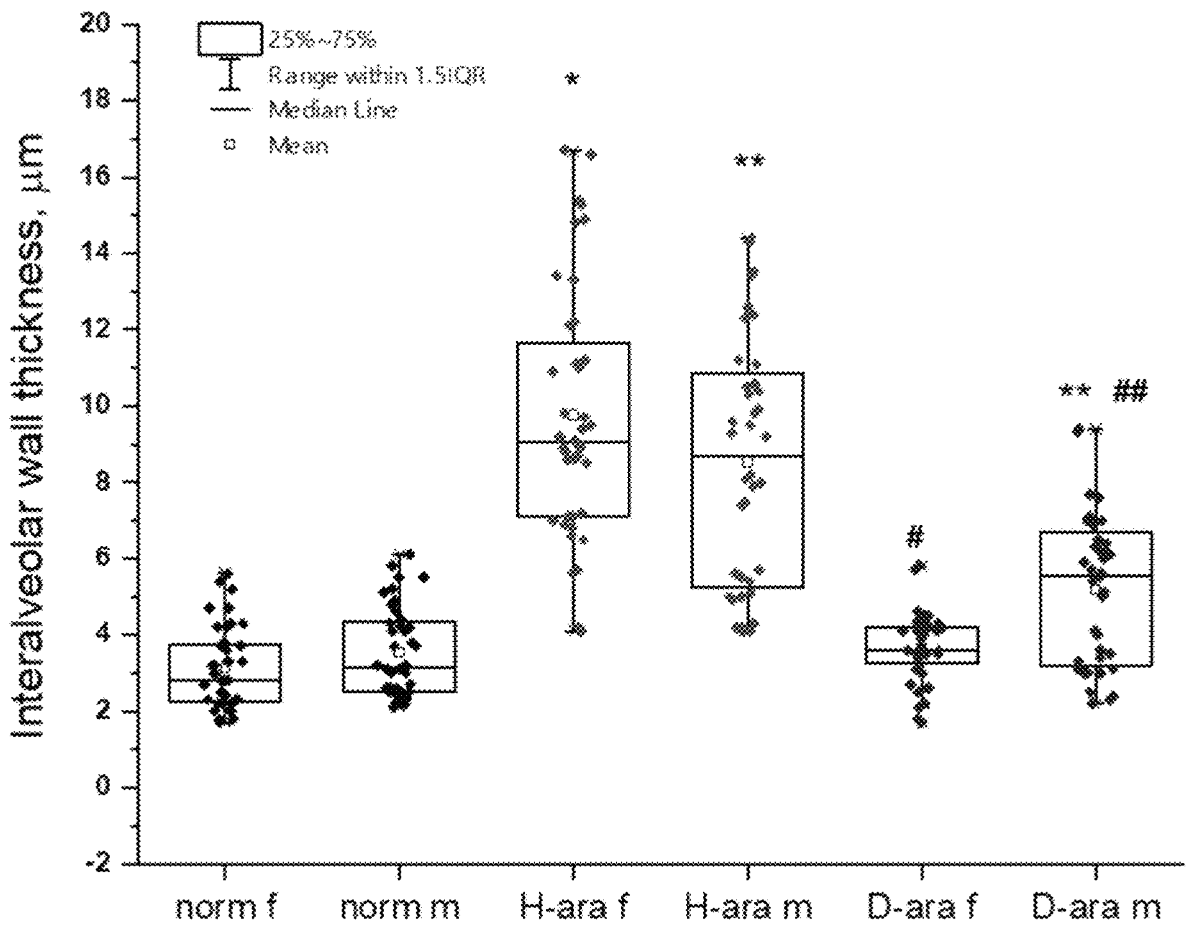
FIG. 11 shows graphs of the thickness of interalveolar septa.

LPS-induced perivascular edema as measured by alveolar wall thickness in mice consuming H-AA contrasted with a significantly milder effect in the male D-AA group, and almost negligible in D-AA females (FIG. 11)

FIG. 11 shows graphs of the thickness of interalveolar septa (μm) after 6 weeks course of H- or D-AA by single intranasal administration of LPS. Norm, male and female mice without LPS treatment. *—p≤0.05, H-AA female mice versus control females; **—p≤0.05, H-AA male mice versus control males; #—p≤0.05, H-AA female mice versus D-AA females; ##—p≤0.05, H-AA male mice versus D-AA males.

Gender-Dependent Differences

Gender differences are well known to be important in models like ALI. For example, female mice respond more severely to *P. aeruginosa*. It is believed that estrogen imparts protective effects on LPS-induced acute lung inflammation and hemorrhagic shock-induced lung injury. Conversely, in infectious models that employed *P. aeruginosa*, females displayed a more robust lung inflammatory response while displaying higher bacterial loads. This underscores the complexities underlying the sex differences in lung immune responses. In our study, the degree of alveolar lumen area changes in both groups of animals also depended on gender: this indicator was significantly lower in females than in males regardless of the form of AA (H or D). Also, in mice on D-AA the severity of changes in thickness of interalveolar septa were significantly higher in males compared to females, correlating well with human cases.

LPS Model of ALI/ARDS

ARDS can result from direct (e.g. pneumonia, acid aspiration) or indirect (e.g. pancreatitis, non-pulmonary sepsis) injury to the lungs. Murine models of direct ALI include those in which agents are delivered intratracheally or intranasally. We induced ALI by intranasal administration of *E. coli* LPS, considered to be a common inductor of lung injury and inflammation. Dietary consumption of H-AA prior to LPS exposure, depending on its duration, did not improve and even aggravated LPS-induced lung tissue damage, including alveolar wall thickening. The damaging effect of LPS observed against the background of dietary D-AA was substantially mitigated. LPS-induced ALI is a well-established model of ARDS. LPS activates NF-KB and then NLRP3 inflammasome, leading to secretion of IL-1β and IL-18, which further triggers inflammation by positive feedback. Although various treatments reportedly protect from acute LPS effects in the murine models like ouabain, and various other compounds like xanthohumol and corylin, the mechanisms of these protective effects are complex.

In contrast, D-PUFA may have a simpler inflammation-reducing mode of action. We have previously demonstrated the inhibitory effect of bis-allylic deuteration of AA on the formation of various pro-inflammatory eicosanoids, while simultaneously inhibiting LPO. This combination of these useful features prompted us to test D-PUFAs in an animal model of inflammation.

D2-LA

In vivo, some of the ingested LA is incorporated into most tissues, with notable exceptions including the retina and brain. Depending on tissue, a variable fraction of LA is converted into AA by enzymatic elongation and desaturation. Neural tissue contains AA but not LA, while in adipose tissue the predominant n-6 species is LA. AA derived from LA through the enzymatic elongation and desaturation is then incorporated into essentially every tissue. Accordingly, dosing mammals on D2-LA would lead to 13,13-D2-AA (FIG. 7A-7D) tissue incorporation. Deuteration at C13 might lead to inhibition of COX1/2 as well as 15-LOX, reducing the level of some pro-inflammatory species as well as LPO. Indeed, our preliminary experiments revealed that although LPS-induced changes in alveolar morphology were found in mice consuming both H- or D2-LA for 6 weeks, the thickness of the interalveolar septum was significantly higher in mice treated with H-LA compared to D2-LA group regardless of gender. Consumption D-AA for 6 weeks led to a greater protective action against LPS-induced interalveolar wall thickening. Moreover, the difference in effects on the alveoli between H- and D-AA diets was even more prominent compared to that of LA isoforms. Based on our preliminary findings, a larger inhibitory effect would be expected from fully deuterated D6-AA compared to D2-AA.

D6-ARA

AA is more efficiently incorporated into tissues when consumed as pre-formed AA rather than as LA, with subsequent metabolic conversion to AA. Nevertheless, within a tissue or pool (e.g., plasma phospholipids), AA levels tend to be controlled within relatively tight limits. One effect of dietary AA is the increase in metabolic turnover of tissue AA.

LPS activates phospholipase A2 leading to the release of free AA into surrounding tissues and blood, modulating overall inflammation on the organism level including sepsis and survival. Accordingly, metabolism of fatty acids may be important for modulation of the acute LPS-induced lung disorder and other conditions. Exogenous oxidized phospholipids induce hyperinflammatory reaction in vitro. Omega-3 PUFAs downregulate inflammation by competing with AA for LOX and COX. Moreover, some oxidation products of long chain PUFAs (e.g., isoprostanes, and neuroprostanes) have interesting biological activities. In mice infected with *P. aeruginosa* survival was im-proved by fish oil supplementation. Surprisingly, these effects can be also seen with AA, whereby a single AA bolus resulted in an increase of superoxide dismutase (SOD), decreased the activity of myeloperoxidase (MPO), reduced malondialdehyde (MDA), lowered lactate dehydrogenase (LDH), alleviated PQ-induced histological damage, and inductions of inflammatory cytokines. This indicates multiple mechanisms of acute chronic responses, perhaps involving pro-resolving action of some of the AA oxidation products, such as asthma-relevant pro-resolving mediators (SPMs) like PGE2, and LXB4

In bacterial infections, the situation is more complex because some microorganisms like common opportunistic pathogen *P. aeruginosa* produce a secreted from of lipoxygenase that oxidizes AA.

AA is the major PUFA involved in inflammation. For example, peripheral blood lymphocytes and monocytes have been reported to have an average AA content of 16-20% of total fatty acids. AA cleaved and released by phospholipase A2 (PLA2) acts as a substrate for COX, LOX and cytochrome P450, yielding pro-inflammatory eicosanoid mediators and regulators such as prostaglandins, leukotrienes, and thromboxanes. Patients with acute COPD have increased AA content in sputum. It is suggested that the severity of emphysematous transformations may also correlate in such patients with high AA levels and COX2 converted mediators. In our study, dietary consumption of D-AA for 6 or 8 weeks significantly decreased endotoxin-induced peribronchial infiltration and improved both alveolar spaces and thickness of interalveolar walls compared to those in mice receiving H-AA. Inflammation and emphysema observed in lungs of mice consuming H-AA was substantially reduced in mice dosed on D-AA, suggesting that i) increased formation of eicosanoids from dietary H-AA and ii) successful displacement of n-6 PUFA in lung and surfactant PLs by D-AA (more stable to both enzymatic and non-enzymatic oxidation) results in decreased production of COX- and LOX-converted mediators as well as decreased PLA2 stimulation by oxidative stress.

Role of Surfactant

Pulmonary surfactant covers the large alveolar surface in all mammalian species, stabilizing the alveoli and preventing them from collapse. It is composed of 10% protein and 90% lipids with a predominance of phospholipids (PLs). Within PL, both acyl chains can be either saturated (no double bonds), monounsaturated (one double bond), or polyunsaturated (i.e., more than one double bond, such as in ARA). The structure of surfactant PLs permits them to modulate the host-pathogen interaction as well as to react on environment-induced oxidative stress. Alterations of the pulmonary surfactant system have long been documented in ARDS or, more generally, in any lung disease with pronounced alveolar inflammation. Large surfactant aggregates from patients with ARDS (including ones associated with lung infection) or pneumonia are characterized by a significant decrease in the percentage of palmitic acid, whereas the relative amount of unsaturated species (including ARA) in PL is significantly increased. Multiple double bonds of polyunsaturated fatty acids make them sensitive to enzymatic and non-enzymatic oxidation, increasing the oxidative stress. Although an intra-alveolar microenvironment is often considered not to be in direct physical contact with the plasma pool, there is some evidence suggesting that systemic metabolic status as well as dietary perturbations can modulate the surfactant Pls. Continuous enteral feeding with a fish oil-enriched formulation fostered significant modulation of the PUFA composition of rat surfactant phospholipids within 72 hours. Thus, the n-6 PUFAs (i.e., 18:2n-6 and 20:4n-6, the precursors of eicosanoids and leukotrienes), were displaced by longer chain n-3 PUFA. The ability of enteral feeding to rapidly modulate the PUFAs composition of surfactant may facilitate timely attenuation of eicosanoid-driven inflammatory processes and decrease the risk of developing ARDS AA, the Yin and Yang of Inflammation Excessive AA is pro-inflammatory under certain conditions of viral and bacterial infections that can be modelled by LPS. LPS treatment promotes inflammation through various mechanisms including the secretion of pro-inflammatory cytokines, eicosanoids and induction of ROS. Following the intranasal administration of LPS, an acute lung inflammation quickly follows. The COVID-19 pandemic is causing severe morbidity and mortality across the globe. Advanced age and other pre-existing conditions result in elevated mortality among COVID-19 patients. Many viruses have high affinity towards receptors found in the lungs. COVID-19, SARS, MERS and influenza (as well as some non-infectious diseases) trigger an immune response, attracting immune cells to the region to attack the virus, resulting in localized inflammation. In some cases, 'cytokine storms' ensue, involving excessive uncontrolled production of pro-inflammatory cytokines/chemokines including IL-6, TNF-α, IFN-γ, IL-2, and IL-7, resulting in hyperinflammation that can be fatal. The immune system of younger people is more reliant on innate mechanisms, so it usually produces lower levels of inflammation-driving cytokines. Additionally, COVID patients demonstrate an increased incidence of thrombotic complications (almost half of the patients admitted to the ICU), even with thromboprophylaxis, further contributing to the high mortality rate from COVID due to pulmonary embolism, strokes, and heart attacks. Indeed, AA as well as its oxidation products are elevated in COVID patients.

There is a complex microflora involvement in diverse reactions connected to inflammation. Gut microbiota is known to be important for lung infection severity. However, we did not observe any significant differences here—this fact points to the importance of molecular mechanisms intrinsic to the mammalian cells and tissues.

Perspectives of Dietary D-AA as a Drug

Traditional approaches to mitigating the adverse effects of eicosanoid-mediated excessive inflammatory response rely on small molecule inhibitors of COX and LOX enzymes. This, however, can lead to an aggravation of pulmonary symptoms like in the case of aspirin-aggravated respiratory disease where dysregulated AA metabolism plays an essential role. Thus, D-AA may represent a milder approach to treatment of inflammatory lung pathologies.

Oral data from human dosing in ongoing clinical trials show an impressive safety record for D2-LA, a metabolic precursor to 13,13-D2-AA. The expected safety of a D-PUFA drug combined with the convenience of oral dosing of D-PUFA gel caps warrant further studies of D-PUFAs as an approach for anti-inflammatory, and possibly preventative, therapy against COVID-19 induced cytokine storm and thrombosis events. Other PUFA emulsions such as Intra-Lipid are formulated in emulsions and dosed I.V. at multiple grams per day safely. One could imagine such a formulation could enable rapid, bolus dosing of the drug upon treatment onset, followed by lipid gel cap oral dosing of D-AA as a continuing therapy. These data present a rationale for further research on D-PUFA technology as an approach to COVID inflammation-associated therapy.

D-AA is less prone to either enzymatic or non-enzymatic oxidation and so is more potent in regulatory interactions that do not require chemical conversions. In high-fat diet mice, AA reduces the LPS-triggered inflammation in macrophages and septic death in mice through binding to MD2. Thus, in addition to its enhanced stability, D-AA may also be beneficial due to its improved metabolism. D-AA may be a viable therapeutic for inflammatory conditions involving enzymatic and non-enzymatic oxidation.

While preferred embodiments of the present disclosure have been shown and described herein, it will be obvious to those skilled in the art that such embodiments are provided by way of example only. It is not intended that the disclosure be limited by the specific examples provided within the specification. While the disclosure has been described with reference to the aforementioned specification, the descriptions and illustrations of the embodiments herein are not meant to be construed in a limiting sense. Numerous variations, changes, and substitutions will now occur to those skilled in the art without departing from the disclosure. Furthermore, it shall be understood that all aspects of the disclosure are not limited to the specific depictions, configurations or relative proportions set forth herein which depend upon a variety of conditions and variables. It should be understood that various alternatives to the embodiments of the disclosure described herein may be employed in practicing the disclosure. It is therefore contemplated that the invention shall also cover any such alternatives, modifications, variations or equivalents. It is intended that the following claims define the scope of the disclosure and that methods and structures within the scope of these claims and their equivalents be covered thereby.

What is claimed is:

1. A method for controlling chronic inflammation in a patient comprising administering an effective amount of arachidonic acid or ester thereof to the patient in need thereof wherein the arachidonic acid or ester thereof that, on average, has at least about 80% of hydrogen atoms at bis-allylic sites replaced by deuterium atoms and that, on average, has no more than about 35% of the hydrogen atoms at mono-allylic sites replaced by deuterium atoms.

2. The method of claim 1, wherein the chronic inflammation causes chronic pain in the patient and administration of an effective amount of the arachidonic acid or ester thereof reduces chronic pain in the patient.

3. The method of claim 1, wherein the amount of the arachidonic acid or ester thereof administered to the patient provides a concentration of the arachidonic acid in red blood cells of the patient of at least about 12% based on total concentration of arachidonic acid in the red blood cells including the arachidonic acid.

4. A pharmaceutical composition comprising a pharmaceutically acceptable excipient and from about 100 mg to about 2,000 mg of an arachidonic acid or an ester thereof that, on average, has at least about 80% of hydrogen atoms at bis-allylic sites replaced by deuterium atoms and, on average, has no more than about 35% of the hydrogen atoms at mono-allylic sites replaced by deuterium atoms.

5. The pharmaceutical composition of claim 4, comprising from about 100 mg to about 1,000 mg of the arachidonic acid or an ester thereof.

6. The pharmaceutical composition of claim 4, comprising from about 100 mg to about 750 mg of the arachidonic acid or an ester thereof.

* * * * *